US009314222B2

(12) United States Patent
Creighton, IV et al.

(10) Patent No.: US 9,314,222 B2
(45) Date of Patent: Apr. 19, 2016

(54) OPERATION OF A REMOTE MEDICAL NAVIGATION SYSTEM USING ULTRASOUND IMAGE

(75) Inventors: Francis M. Creighton, IV, St. Louis, MO (US); Rogers C. Ritter, Charlottesville, VA (US); Raju R. Viswanathan, St. Louis, MO (US); Nathan Kastelein, St. Louis, MO (US); Jeffrey M. Garibaldi, St. Louis, MO (US); William Flickinger, Lino Lakes, MN (US)

(73) Assignee: STEREOTAXIS, INC., St. Louis, MO (US)

( * ) Notice: Subject to any disclaimer, the term of this patent is extended or adjusted under 35 U.S.C. 154(b) by 1333 days.

(21) Appl. No.: 12/205,137

(22) Filed: Sep. 5, 2008

(65) Prior Publication Data
US 2009/0062646 A1 Mar. 5, 2009

Related U.S. Application Data

(63) Continuation-in-part of application No. 11/483,398, filed on Jul. 7, 2006, now abandoned.

(60) Provisional application No. 60/697,321, filed on Jul. 7, 2005, provisional application No. 60/697,823, filed on Jul. 8, 2005, provisional application No. 60/698,522, filed on Jul. 12, 2005.

(51) Int. Cl.
*A61B 5/05* (2006.01)
*A61B 8/08* (2006.01)
*A61B 5/06* (2006.01)
*A61B 8/00* (2006.01)

(52) U.S. Cl.
CPC ............... *A61B 8/0833* (2013.01); *A61B 5/062* (2013.01); *A61B 8/4416* (2013.01)

(58) Field of Classification Search
USPC .................. 600/424, 427, 437, 462, 466, 467; 128/899
See application file for complete search history.

(56) References Cited

U.S. PATENT DOCUMENTS

| 5,654,864 | A | 8/1997 | Ritter et al. |
| 5,931,818 | A | 8/1999 | Werp et al. |
| 6,014,580 | A | 1/2000 | Blume et al. |
| 6,015,414 | A | 1/2000 | Werp et al. |
| 6,128,174 | A | 10/2000 | Ritter et al. |
| 6,148,823 | A | 11/2000 | Hastings |
| 6,152,933 | A | 11/2000 | Werp et al. |
| 6,157,853 | A | 12/2000 | Blume et al. |
| 6,212,419 | B1 | 4/2001 | Blume et al. |
| 6,241,671 | B1 | 6/2001 | Ritter et al. |
| 6,292,678 | B1 | 9/2001 | Hall et al. |

(Continued)

OTHER PUBLICATIONS

Magnetic Manipulation Instrumentation for Medical Physics Research Authors: G. T. Gillies, r. C. Ritter, W. C. Broaddus, M. S. Grady, M. A. Howard, III, R. G. McNeil 1994 American Institute of Physics Rev. Sci. Instrum. vol. 65, No. 3, Mar. 1994 pp. 533-562.

*Primary Examiner* — Tse Chen
*Assistant Examiner* — Jason Ip
(74) *Attorney, Agent, or Firm* — Harness, Dickey & Pierce, P.L.C.

(57) ABSTRACT

A method of operating a remote medical navigation system using ultrasound, employs ultrasound imaging from a medical device to supplement or to replace conventional x-ray imaging of the operating region during navigation.

14 Claims, 37 Drawing Sheets

(56) References Cited

U.S. PATENT DOCUMENTS

| | | | |
|---|---|---|---|
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,306,097 B1* | 10/2001 | Park et al. | 600/466 |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,459,924 B1 | 10/2002 | Creighton, IV et al. | |
| 6,468,265 B1* | 10/2002 | Evans et al. | 606/1 |
| 6,475,223 B1 | 11/2002 | Werp et al. | |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,527,782 B2 | 3/2003 | Hogg et al. | |
| 6,537,196 B1 | 3/2003 | Creighton, IV et al. | |
| 6,542,766 B2 | 4/2003 | Hall et al. | |
| 6,562,019 B1 | 5/2003 | Sell | |
| 6,630,879 B1 | 10/2003 | Creighton, IV et al. | |
| 6,662,034 B2 | 12/2003 | Segner et al. | |
| 6,669,635 B2* | 12/2003 | Kessman et al. | 600/437 |
| 6,677,752 B1 | 1/2004 | Creighton, IV et al. | |
| 6,702,804 B1 | 3/2004 | Ritter et al. | |
| 6,733,511 B2 | 5/2004 | Hall et al. | |
| 6,755,816 B2 | 6/2004 | Ritter et al. | |
| 6,817,364 B2 | 11/2004 | Garibaldi et al. | |
| 6,834,201 B2 | 12/2004 | Gillies et al. | |
| 6,902,528 B1 | 6/2005 | Garibaldi et al. | |
| 6,911,026 B1 | 6/2005 | Hall et al. | |
| 6,940,379 B2 | 9/2005 | Creighton | |
| 6,968,846 B2 | 11/2005 | Viswanathan | |
| 6,975,197 B2 | 12/2005 | Creighton, IV | |
| 6,980,843 B2 | 12/2005 | Eng et al. | |
| 7,008,418 B2 | 3/2006 | Hall et al. | |
| 7,010,338 B2 | 3/2006 | Ritter et al. | |
| 7,017,584 B2 | 3/2006 | Garibaldi et al. | |
| 7,019,610 B2 | 3/2006 | Creighton, IV et al. | |
| 7,020,512 B2 | 3/2006 | Ritter et al. | |
| 7,066,924 B1 | 6/2006 | Garibaldi et al. | |
| 7,137,976 B2 | 11/2006 | Ritter et al. | |
| 7,161,453 B2 | 1/2007 | Creighton, IV | |
| 7,189,198 B2 | 3/2007 | Harburn et al. | |
| 7,190,819 B2 | 3/2007 | Viswanathan | |
| 7,211,082 B2 | 5/2007 | Hall et al | |
| 7,248,914 B2 | 7/2007 | Hastings et al. | |
| 7,264,584 B2 | 9/2007 | Ritter et al. | |
| 7,276,044 B2 | 10/2007 | Ferry et al. | |
| 7,286,034 B2 | 10/2007 | Creighton | |
| 7,305,263 B2 | 12/2007 | Creighton, IV | |
| 7,313,429 B2 | 12/2007 | Creighton, IV et al. | |
| 7,341,063 B2 | 3/2008 | Garibaldi et al. | |
| 7,346,379 B2 | 3/2008 | Eng et al. | |
| 7,389,778 B2 | 6/2008 | Sabo et al. | |
| 7,416,335 B2 | 8/2008 | Munger | |
| 2001/0038683 A1 | 11/2001 | Ritter et al. | |
| 2002/0019644 A1 | 2/2002 | Hastings et al. | |
| 2002/0077543 A1* | 6/2002 | Grzeszczuk et al. | 600/424 |
| 2002/0100486 A1 | 8/2002 | Creighton, IV et al. | |
| 2003/0125752 A1 | 7/2003 | Werp et al. | |
| 2003/0231789 A1* | 12/2003 | Willis et al. | 382/128 |
| 2004/0006301 A1 | 1/2004 | Sell et al. | |
| 2004/0019447 A1 | 1/2004 | Shachar | |
| 2004/0030244 A1 | 2/2004 | Garibaldi et al. | |
| 2004/0064153 A1 | 4/2004 | Creighton, IV et al. | |
| 2004/0068173 A1 | 4/2004 | Viswanathan | |
| 2004/0133130 A1 | 7/2004 | Ferry et al. | |
| 2004/0147829 A1 | 7/2004 | Segner et al. | |
| 2004/0157082 A1 | 8/2004 | Ritter et al. | |
| 2004/0158972 A1 | 8/2004 | Creighton, IV et al. | |
| 2004/0186376 A1 | 9/2004 | Hogg et al. | |
| 2004/0249262 A1 | 12/2004 | Werp et al. | |
| 2004/0260172 A1 | 12/2004 | Ritter et al. | |
| 2004/0267106 A1 | 12/2004 | Segner et al. | |
| 2005/0004585 A1 | 1/2005 | Hall et al. | |
| 2005/0020911 A1 | 1/2005 | Viswanathan et al. | |
| 2005/0021063 A1 | 1/2005 | Hall et al. | |
| 2005/0033162 A1 | 2/2005 | Garibaldi et al. | |
| 2005/0065435 A1 | 3/2005 | Rauch et al. | |
| 2005/0096589 A1 | 5/2005 | Shachar | |
| 2005/0113812 A1 | 5/2005 | Viswanathan et al. | |
| 2005/0119556 A1 | 6/2005 | Gillies et al. | |
| 2005/0119687 A1 | 6/2005 | Dacey, Jr. et al. | |
| 2005/0182315 A1 | 8/2005 | Ritter et al. | |
| 2005/0256398 A1 | 11/2005 | Hastings et al. | |
| 2005/0273130 A1 | 12/2005 | Sell | |
| 2006/0004382 A1 | 1/2006 | Hogg et al. | |
| 2006/0009735 A1 | 1/2006 | Viswanathan et al. | |
| 2006/0025676 A1 | 2/2006 | Viswanathan et al. | |
| 2006/0025679 A1 | 2/2006 | Viswanathan et al. | |
| 2006/0025719 A1 | 2/2006 | Viswanathan et al. | |
| 2006/0036125 A1 | 2/2006 | Viswanathan et al. | |
| 2006/0036163 A1 | 2/2006 | Viswanathan | |
| 2006/0036213 A1 | 2/2006 | Viswanathan et al. | |
| 2006/0041178 A1 | 2/2006 | Viswanathan et al. | |
| 2006/0041179 A1 | 2/2006 | Viswanathan et al. | |
| 2006/0041180 A1 | 2/2006 | Viswanathan et al. | |
| 2006/0041181 A1 | 2/2006 | Viswanathan et al. | |
| 2006/0041245 A1 | 2/2006 | Ferry et al. | |
| 2006/0058646 A1 | 3/2006 | Viswanathan | |
| 2006/0074297 A1 | 4/2006 | Viswanathan | |
| 2006/0079745 A1 | 4/2006 | Viswanathan | |
| 2006/0079812 A1 | 4/2006 | Viswanathan | |
| 2006/0094956 A1 | 5/2006 | Viswanathan | |
| 2006/0100505 A1 | 5/2006 | Viswanathan | |
| 2006/0114088 A1 | 6/2006 | Shachar | |
| 2006/0116633 A1 | 6/2006 | Shachar | |
| 2006/0144407 A1 | 7/2006 | Aliberto et al. | |
| 2006/0144408 A1 | 7/2006 | Ferry | |
| 2006/0270915 A1 | 11/2006 | Ritter et al. | |
| 2006/0270948 A1 | 11/2006 | Viswanathan et al. | |
| 2006/0278248 A1 | 12/2006 | Viswanathan | |
| 2007/0016010 A1 | 1/2007 | Creighton, IV et al. | |
| 2007/0016131 A1 | 1/2007 | Munger et al. | |
| 2007/0019330 A1 | 1/2007 | Wolfersberger | |
| 2007/0021731 A1 | 1/2007 | Garibaldi et al. | |
| 2007/0021742 A1 | 1/2007 | Viswanathan | |
| 2007/0021744 A1 | 1/2007 | Creighton, IV | |
| 2007/0032746 A1 | 2/2007 | Sell | |
| 2007/0038064 A1 | 2/2007 | Creighton, IV | |
| 2007/0038065 A1 | 2/2007 | Creighton, IV et al. | |
| 2007/0038074 A1 | 2/2007 | Ritter et al. | |
| 2007/0038410 A1 | 2/2007 | Tunay | |
| 2007/0040670 A1 | 2/2007 | Viswanathan | |
| 2007/0043455 A1 | 2/2007 | Viswanathan et al. | |
| 2007/0049909 A1 | 3/2007 | Munger | |
| 2007/0055124 A1 | 3/2007 | Viswanathan et al. | |
| 2007/0055130 A1 | 3/2007 | Creighton, IV | |
| 2007/0060829 A1 | 3/2007 | Pappone | |
| 2007/0060916 A1 | 3/2007 | Pappone | |
| 2007/0060962 A1 | 3/2007 | Pappone | |
| 2007/0060966 A1 | 3/2007 | Pappone | |
| 2007/0060992 A1 | 3/2007 | Pappone | |
| 2007/0062546 A1 | 3/2007 | Viswanathan et al. | |
| 2007/0062547 A1 | 3/2007 | Pappone | |
| 2007/0073288 A1 | 3/2007 | Hall et al. | |
| 2007/0123964 A1 | 5/2007 | Davies et al. | |
| 2007/0135804 A1 | 6/2007 | Ritter | |
| 2007/0137656 A1 | 6/2007 | Viswanathan | |
| 2007/0146106 A1 | 6/2007 | Creighton, IV | |
| 2007/0149946 A1 | 6/2007 | Viswanathan | |
| 2007/0161882 A1 | 7/2007 | Pappone | |
| 2007/0167720 A1 | 7/2007 | Viswanathan | |
| 2007/0179492 A1 | 8/2007 | Pappone | |
| 2007/0197899 A1 | 8/2007 | Ritter et al. | |
| 2007/0197901 A1 | 8/2007 | Viswanathan | |
| 2007/0197906 A1 | 8/2007 | Ritter | |
| 2007/0225589 A1 | 9/2007 | Viswanathan | |
| 2007/0250041 A1 | 10/2007 | Werp | |
| 2007/0270686 A1 | 11/2007 | Ritter et al. | |

(56) References Cited

U.S. PATENT DOCUMENTS

| | | |
|---|---|---|
| 2008/0004595 A1 | 1/2008 | Viswanthan |
| 2008/0006280 A1 | 1/2008 | Alberto et al. |
| 2008/0015427 A1 | 1/2008 | Kastelein et al. |
| 2008/0015670 A1 | 1/2008 | Pappone |
| 2008/0016677 A1 | 1/2008 | Creighton, IV |
| 2008/0016678 A1 | 1/2008 | Creighton, IV et al. |
| 2008/0039705 A1 | 2/2008 | Viswanathan |
| 2008/0039830 A1 | 2/2008 | Munger et al. |
| 2008/0043902 A1 | 2/2008 | Viswanathan |
| 2008/0045892 A1 | 2/2008 | Ferry et al. |
| 2008/0047568 A1 | 2/2008 | Ritter et al. |
| 2008/0055239 A1 | 3/2008 | Garibaldi et al. |
| 2008/0058608 A1 | 3/2008 | Garibaldi et al. |
| 2008/0058609 A1 | 3/2008 | Garibaldi et al. |
| 2008/0058963 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0064969 A1 | 3/2008 | Kastelein |
| 2008/0065061 A1 | 3/2008 | Viswanathan |
| 2008/0077007 A1 | 3/2008 | Hastings et al. |
| 2008/0092993 A1 | 4/2008 | Creighton, IV |
| 2008/0097200 A1 | 4/2008 | Blume et al. |
| 2008/0114335 A1 | 5/2008 | Flickinger et al. |
| 2008/0132910 A1 | 6/2008 | Pappone |
| 2008/0200913 A1 | 8/2008 | Viswanathan |
| 2008/0208912 A1 | 8/2008 | Garibaldi |
| 2008/0228065 A1 | 9/2008 | Viswanathan et al. |
| 2008/0228068 A1 | 9/2008 | Viswanathan et al. |
| 2008/0287909 A1 | 11/2008 | Viswanathan et al. |
| 2008/0294232 A1 | 11/2008 | Viswanathan |
| 2008/0312673 A1 | 12/2008 | Viswanathan et al. |
| 2008/0319303 A1 | 12/2008 | Sabo et al. |
| 2009/0012821 A1 | 1/2009 | Besson et al. |

* cited by examiner

OPERATION OF A REMOTE MEDICAL NAVIGATION SYSTEM USING ULTRASOUND IMAGE

CROSS-REFERENCE TO RELATED APPLICATIONS

This application is a continuation in part of U.S. patent application Ser. No. 11/483,398 filed Jul. 7, 2006, now abandoned, which claims the benefit of U.S. Provisional Patent Application Ser. No. 60/697,321, filed Jul. 7, 2005, Ser. No. 60/697,823 filed Jul. 8, 2005, and Ser. No. 60/698,522 filed Jul. 12, 2005, the entire disclosures of which are incorporated herein by reference.

BACKGROUND OF THE INVENTION

This invention relates to the operation of remote medical navigation systems, and in particular to the operation of such systems using ultrasound imaging, preferably with reduced reliance on x-ray imaging.

Remote navigation systems have been developed that permit the distal end of a medical device disposed in a subject's body to be remotely controlled so that the device can be navigated through the body, for example through a subject's vasculature. Such systems include magnetic navigation systems which use one or more external source magnets (either permanent magnets of electromagnets) to create a magnetic field in a direction that causes magnetically responsive elements on the medical device to align in a desired direction. Such systems also include mechanical systems which use push wires and pull wires, or gears, or other elements to orient a medical device directly or to orient a guide that orients the medical device.

While remote medical navigation systems are making navigation of medical devices through the body faster and easier and are finding an increasing number of applications, physicians are accustomed to watching the procedure on fluoroscopic images in order to control the medical device. This can result in significant exposures to subjects and even greater exposures to physicians and healthcare practitioners who might participate in several procedures per day.

Another significant advantage of some of the embodiments of the present invention derives from removing live fluoroscopy in favor of ultrasound guidance during a magnetic navigation, which allows the field source magnets to be much closer to the subject, since ultrasound equipment is smaller and space for x-ray equipment and beams need not be interfered with. The much closer navigation source magnets can be drastically reduced in size and cost. In addition, suite and equipment shielding will be greatly reduced in complexity and expense, as will floor support needed for the large source magnets such as the Niobe magnet (available from Stereotaxis, Inc., St. Louis, Mo.). Even when fluoroscopy is used in an aiding fashion, it can be removed during the magnetic navigation to retain some or all of these advantages.

SUMMARY OF THE INVENTION

The present invention relates to the control of remote medical navigation systems, and in particular to the control of remote medical navigation systems using ultrasound imaging. The use of ultrasound can help improve control of the medical navigation, and in at least some instances may reduce or eliminate the need for x-ray imaging during navigation, especially during magnetic navigation.

In accordance with one aspect, embodiments of the invention provide a method of operating a remote navigation system that orients the distal end of a medical device in an operating region in a subject using external ultrasound imaging. The methods of these embodiments comprise ultrasonically imaging the operating region; registering the ultrasonic imaging system relative to the remote navigation system; displaying an image of the operating region obtained from the ultrasonic imaging; indicating a desired direction of movement on the displayed image; controlling the remote navigation system to orient the distal end of the medical device in the desired direction of movement.

In accordance with another aspect of this invention, embodiments of the invention provide a method of operating a remote navigation system that orients the distal end of a medical device in an operating region in a subject using external ultrasound imaging. The methods of these embodiments comprise ultrasonically imaging the operating region; registering the ultrasonic imaging system relative to the remote navigation system; displaying an image of the operating region obtained from the ultrasonic imaging; indicating a desired destination for the distal end of the medical device; and controlling the remote navigation system to orient the distal end of the medical device in a direction to reach the desired destination.

In accordance with another aspect of this invention, embodiments of the invention provide a remote medical navigation system for remotely orienting the distal end of a medical device in an operating region in a subject. The systems of these embodiments comprise a subject support; and a pair of generally opposed magnet units disposed on opposite sides of a subject on the support. Each magnet unit comprises a magnet and a support for moving the magnet to selectively change the direction of a magnet field applied at an operating point between the magnet units. At least one of the subject support and the pair of magnet units is movable to change the location of the operating point in a subject on the subject support.

In accordance with another aspect of this invention, embodiments of the invention provide a remote medical navigation system for remotely orienting the distal end of a medical device in an operating region in a subject. The systems of these embodiments comprise a subject support; and three or more of generally disposed magnet units located about a subject and in a plane. Each magnet unit comprises a magnet and a support for moving the magnet to selectively change the direction of a magnet field applied at an operating point between the magnet units. At least one of the subject support and the set of magnet units is movable to change the location of the operating point in a subject on the subject support.

In accordance with another aspect of this invention, embodiments of the invention provide a remote medical navigation system for remotely orienting the distal end of a medical device in an operating region in a subject. The systems of these embodiments comprise a subject support; and at least two magnet units located about a subject, preferably not in a plane. Each magnet unit comprises a magnet and a support for moving the magnet to selectively change the direction of a magnet field applied at an operating point generally between the magnet units. At least one of the subject support and the set of magnet units is movable to change the location of the operating point in a subject on the subject support.

In accordance with another aspect of this invention, embodiments of the invention provide a remote medical navigation system for remotely orienting the distal end of a medical device in an operating region in a subject. The systems of these embodiments comprise a subject support; and a pair of generally opposed magnet units disposed on opposite sides of a subject on the support. Each magnet unit comprises a magnet and a support for moving the magnet to selectively change the direction of a magnet field applied at an operating point between the magnet units, one of the pair of magnet units being disposed above the subject support, and the other of the pair of magnet units being disposed below the subject support. A display is provided on the on the magnet unit disposed above the subject support for displaying an image of the subject on the subject support.

In accordance with another aspect of this invention, embodiments of the invention provide a method of navigating the distal end of a medical device through a body lumen. The method of these embodiments comprises ultrasonically imaging the portion of the body lumen surrounding the distal end of the medical device; and comparing the image of the portion of the body lumen with a preoperative three dimensional reconstruction of the body lumen to locate the distal end of the medical device relative to the preoperative reconstruction. The method more preferably comprises creating a three-dimensional reconstruction of the body lumen; ultrasonically imaging the portion of the body lumen surrounding the distal end of the medical device; comparing the image of the portion of the body lumen with a three dimensional reconstruction of the body lumen to locate the distal end of the medical device relative to the preoperative reconstruction; orienting the distal end of the medical device and advancing the medical device; and, advancing the medical device in the body lumen.

In accordance with another aspect of this invention, embodiments of the invention provide a method of navigating the distal end of a medical device through a body lumen. The method of these embodiments comprises ultrasonically imaging the portion of the body lumen surrounding the distal end of the medical device; displaying an image of the portion of the body lumen surrounding the distal end of the medical device; orienting the displayed image by comparing the image of the portion of the body lumen with a three dimensional reconstruction of the body lumen to locate the distal end of the medical device relative to the preoperative reconstruction.

In accordance with another aspect of this invention, embodiments of the invention provide a method of navigating the distal end of a medical device through a body lumen. The method of these embodiments comprises ultrasonically imaging the portion of the body lumen surrounding the distal end of the medical device; displaying an image of the portion of the body lumen surrounding the distal end of the medical device; orienting the displayed image by comparing the image of the portion of the body lumen with a three dimensional reconstruction of the body lumen to locate the distal end of the medical device relative to the preoperative reconstruction.

Another aspect of this invention provides means of aligning or registering internally acquired ultrasound images to a remote navigation system, and using such alignment or registration information to intuitively control a remotely operated medical device within the anatomical region of interest. This is accomplished by identifying the ultrasound catheter and one or more anatomical features or other devices in a pair of Fluoroscopic views as described below.

Another aspect of this invention is the fusion of registered ultrasound image data with other intra-operative x-ray data or pre-operatively or intra-operatively acquired 3D image data, and the use of such fused data to drive a remotely controlled medical device to a desired anatomical target.

Another aspect of the present invention is the use of a (spatially) localized ultrasound imaging catheter, with the ultrasound imaging system integrated with a remote navigation system. In this case, the ultrasound catheter provides a 3D reconstruction of the anatomy of interest that could include a remotely navigated medical device. The 3D image is displayed in cut-away or endoscopic form such that the device is clearly visible and is registered with the remote navigation system as described above. A 3D wand or stylus device, possibly incorporating haptic feedback, is used to control the movements of the remotely navigated medical device in intuitive fashion. Thus, since the ultrasound and remote navigation systems have been registered or aligned, movements of the wand can be directly converted to suitable changes of control variables such that the medical device moves in spatial concordance with the movements of the wand.

Another aspect of the present invention is the control of the orientation of an ultrasound imaging catheter used to image a medical device within an anatomical region of interest, such that as the medical device moves, it continues to stay within the field of view of the ultrasound imaging catheter.

Thus various embodiments of the methods and systems of this invention provide for the operation of remote medical navigation systems using ultrasound to enhance conventional x-ray imaging or in some cases replace x-ray imaging. Selected embodiments of the methods and systems of the present invention provide for fast and accurate navigation with or without x-ray imaging. These and other features and advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figure 1:
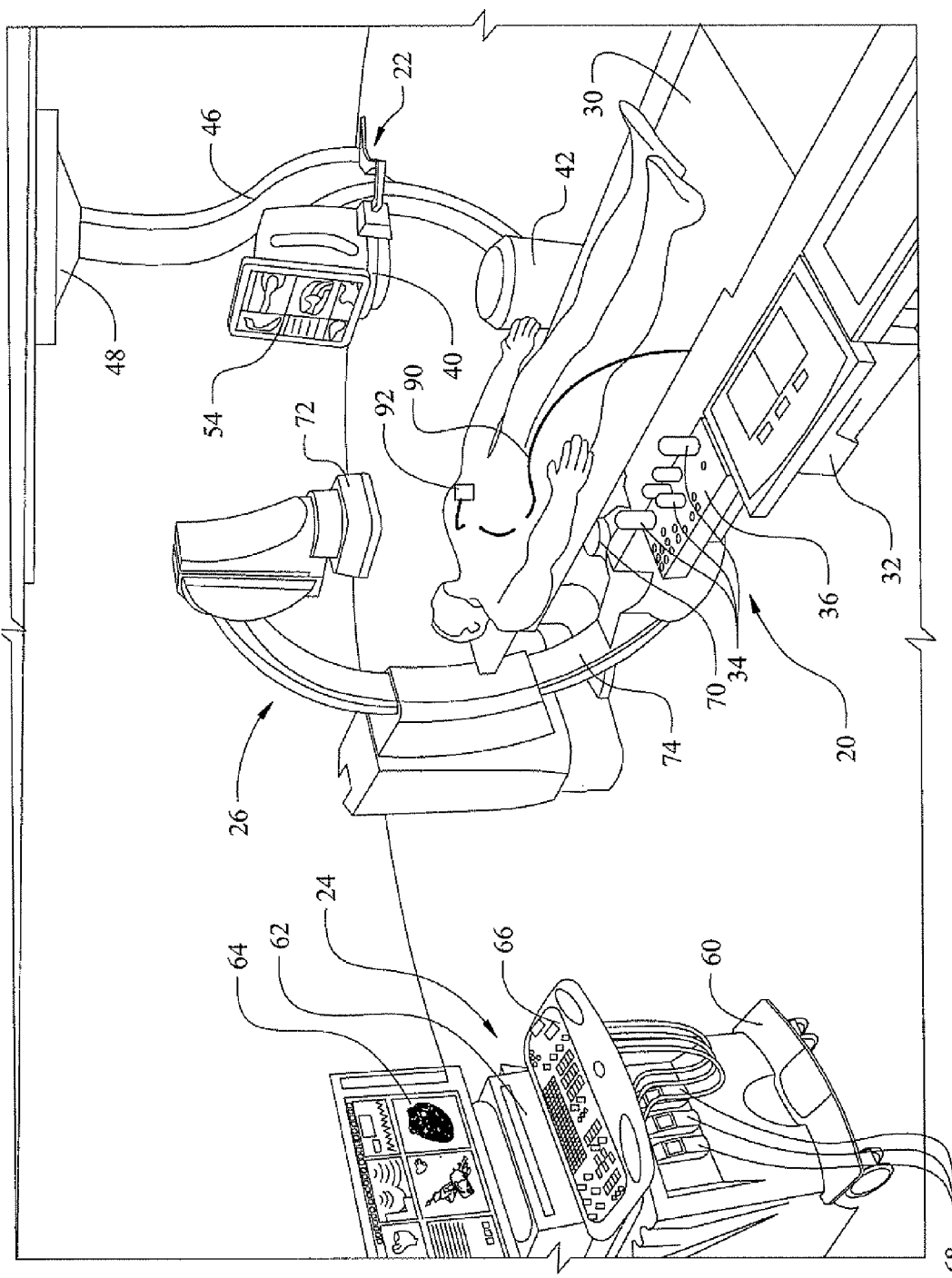
FIG. 1 is a perspective view of a procedure suite in accordance with a first preferred embodiment, including a remote navigation system, x-ray imaging system, and ultrasound imaging system constructed according to the principles of this invention.
Figure 2:
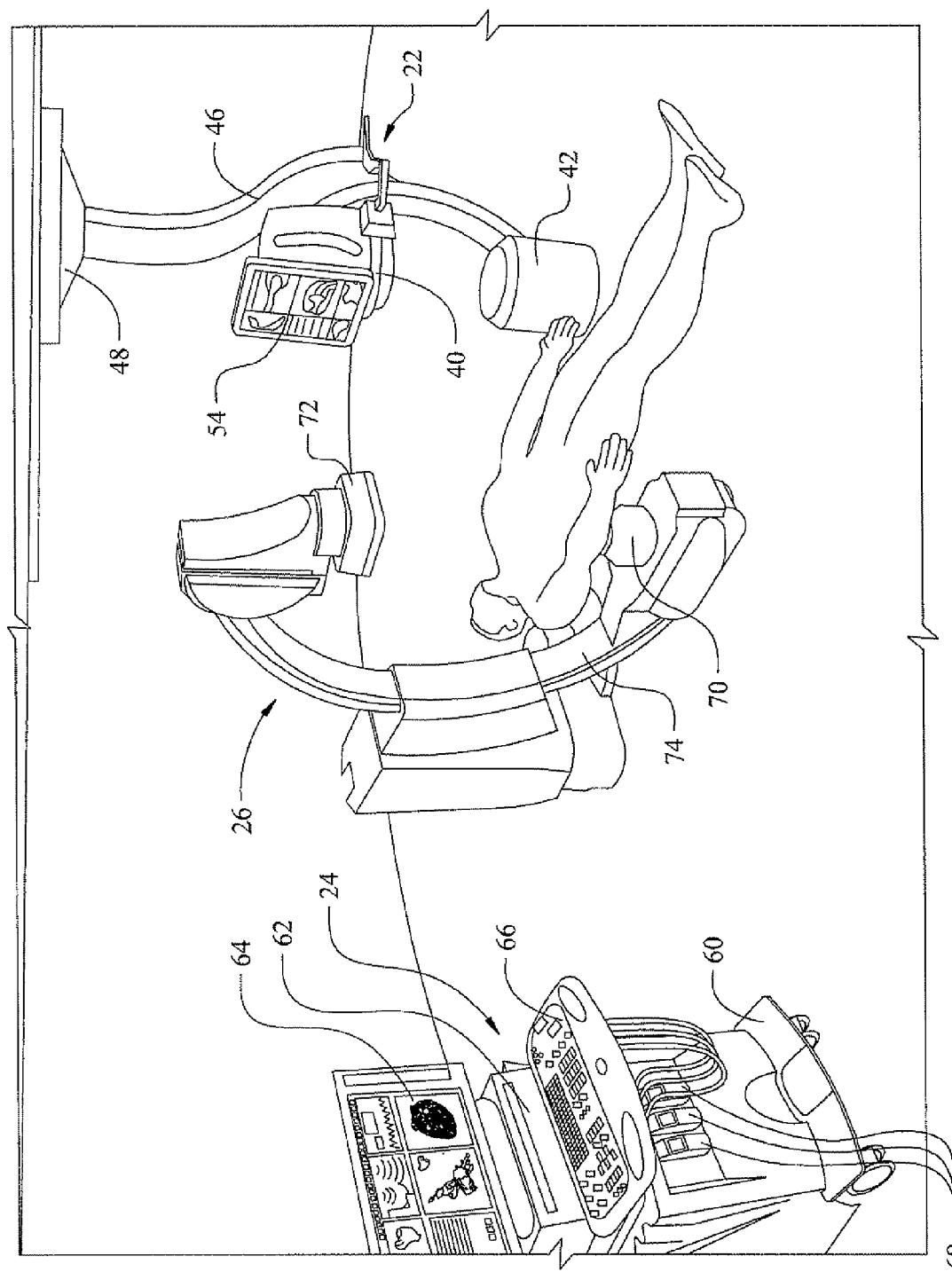
FIG. 2 is a perspective view of the procedure suite of the first embodiment, with the subject support removed to show the other components in the suite.
Figure 3:
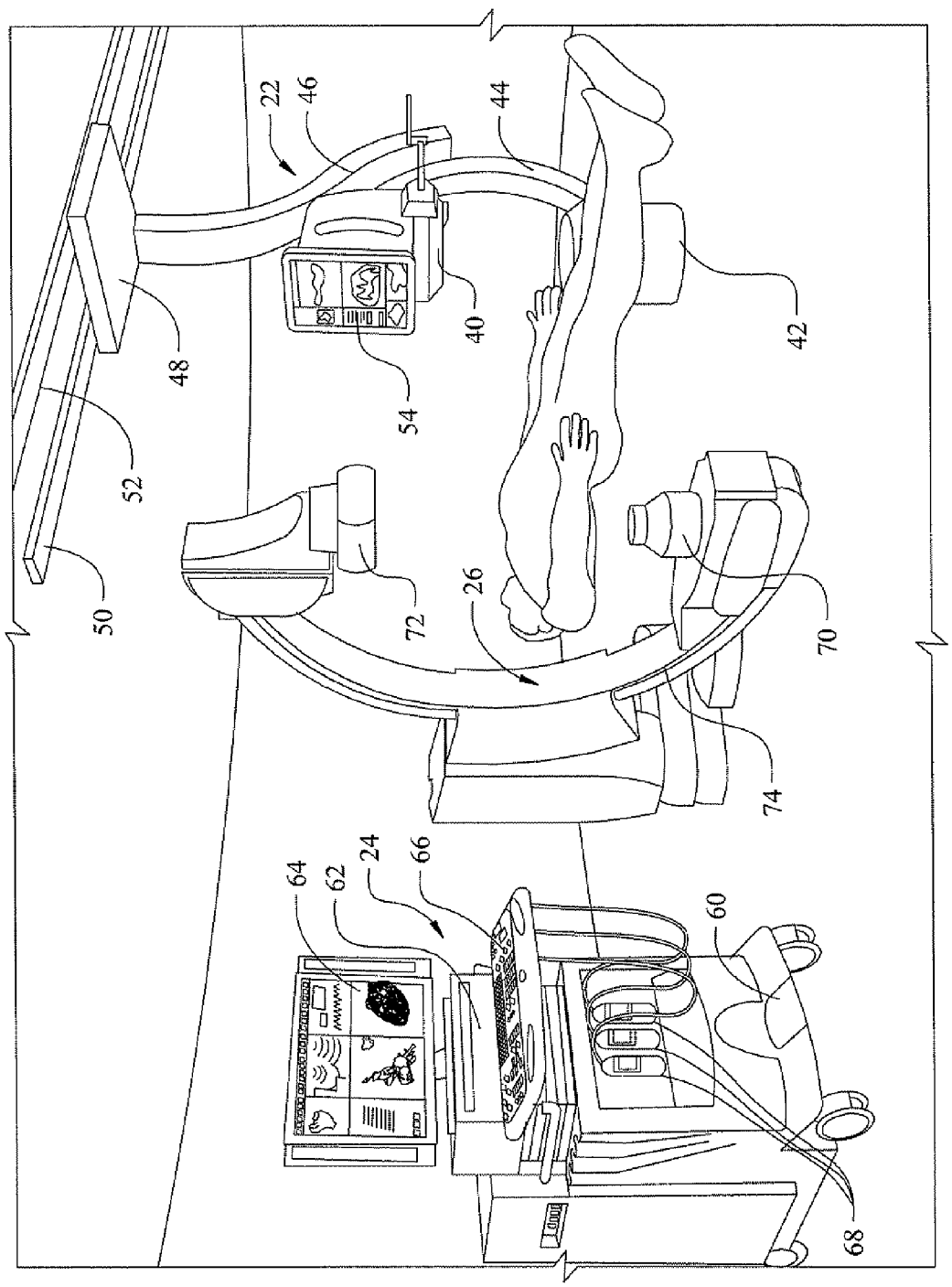
FIG. 3 is a perspective view of the procedure suite of the first embodiment, with the subject support removed to show the other components in the suite.

A procedure suite in accordance with a first embodiment of this invention is shown in FIGS. 1 and 2. As shown in FIGS. 1 and 2 the suite comprises a subject support 20, a remote navigation system 22 for remotely orienting the distal end of a medical device in an operating region in a subject on the subject support; an ultrasound imaging system 24 for ultrasonically imaging the operating region in a subject on the subject support; and an x-ray imaging system 26 for imaging the operating region in a subject on the subject support.

The subject support 20 preferably comprises a bed 30, and a base 32 for movably supporting the bed. In one version of the preferred embodiment the base supports the bed for movement in three mutually perpendicular directions, e.g. axially, transversely, and vertically. This allows a physician or other health care worker to control the position of the operating point of the remote navigation system 22 relative to the subject, and preferably also allows the physician or other health care worker to move the subject between the x-ray imaging system 26 and the remote navigation system 22. In another version of the preferred embodiment, the base 32 supports the bed 30 for rotation about a generally vertical axis so that the subject can be pivoted between the imaging system and the remote navigation system. A plurality of controls 34 can be provided adjacent the bed, so that the attending physician or other health care worker can conveniently control the procedure suite and its various components.

The remote navigation system 22 is adapted for remotely orienting the distal end of a medical device disposed in an operating region in a subject on the subject support 20. In this preferred embodiment the remote navigation system 22 is a remote magnetic navigation system, having at least first and second source magnet units 40 and 42 capable of creating a magnetic field in any direction in the operating region in the subject on the support 20. While shown and described with two magnet units, the invention is not so limited, and more than two magnet units, e.g., three units spaced 120° apart or in some other configuration, or any other number or arrangement of magnet units can be used as appropriate. The magnet units 40 and 42 preferably comprise compound permanent magnets which when rotated and pivoted can project a magnetic field at an operating point between them of sufficient strength to orient one or more magnetically responsive elements on the distal end of the medical device. These magnetically responsive elements can be made of a permanent magnetic material or a permeable magnetic material, or even electromagnetic coils.

As shown the Figures, magnet units 40 and 42 are preferably disposed on opposite sides of the subject, and in this first preferred embodiment are disposed above and below the subject. The magnet units 40 and 42 are preferably mounted on a C-shaped frame 44 for maintaining the relative spacing and orientation of the units. The C-shaped frame 44 can be suspended from a bracket 46 carried on a cart 48 on ceiling tracks 50 and 52. This allows the remote navigation system 22 to be moved toward and away from the subject instead of or in addition to the motion provided by the subject support 20.

The remote navigation system 22 preferably includes at least a display 54 mounted adjacent the magnet unit 40. The display 54 may be a simple LCD or similar flat panel display for displaying information from the computer controlling the remote navigation system, and/or other information such as from the ultrasonic imaging system 24 or the x-ray imaging system 26. The display 54 may be a touch screen display to facilitate inputs to control the remote navigation system 22, and to manipulate the images displayed on the display. At least one speaker (not shown) can be integrated with the display 54 or it can be mounted separately. Similarly a microphone (not shown) can be integrated with the display 54, or it can be mounted separately. The microphone can be used to orally control the remote navigation system 22, and/or as part of a communication (e.g. telephone or intercom) system.

While in these preferred embodiments the remote navigation system 22 is a magnetic navigation system, the invention is not so limited and the remote navigation system could be a mechanical system, such as one employing pull wires or push wires, or combinations thereof, or gears, or other elements, or the remote navigation could be some other system for remotely orienting the distal tip of the medical device.

The external ultrasound imaging system 24 is preferably mounted on a wheeled cart 60 and includes a computer 62 with a display 64 and an input device such as a keyboard 66. One or more ultrasound transducers 68 are provided to ultrasonically image the operating region of a subject on the support 20. In addition one or more inputs (not shown) can be provided for connecting to ultrasonic catheters for internal ultrasonic imaging of the operating region in the subject.

Figure 4A:
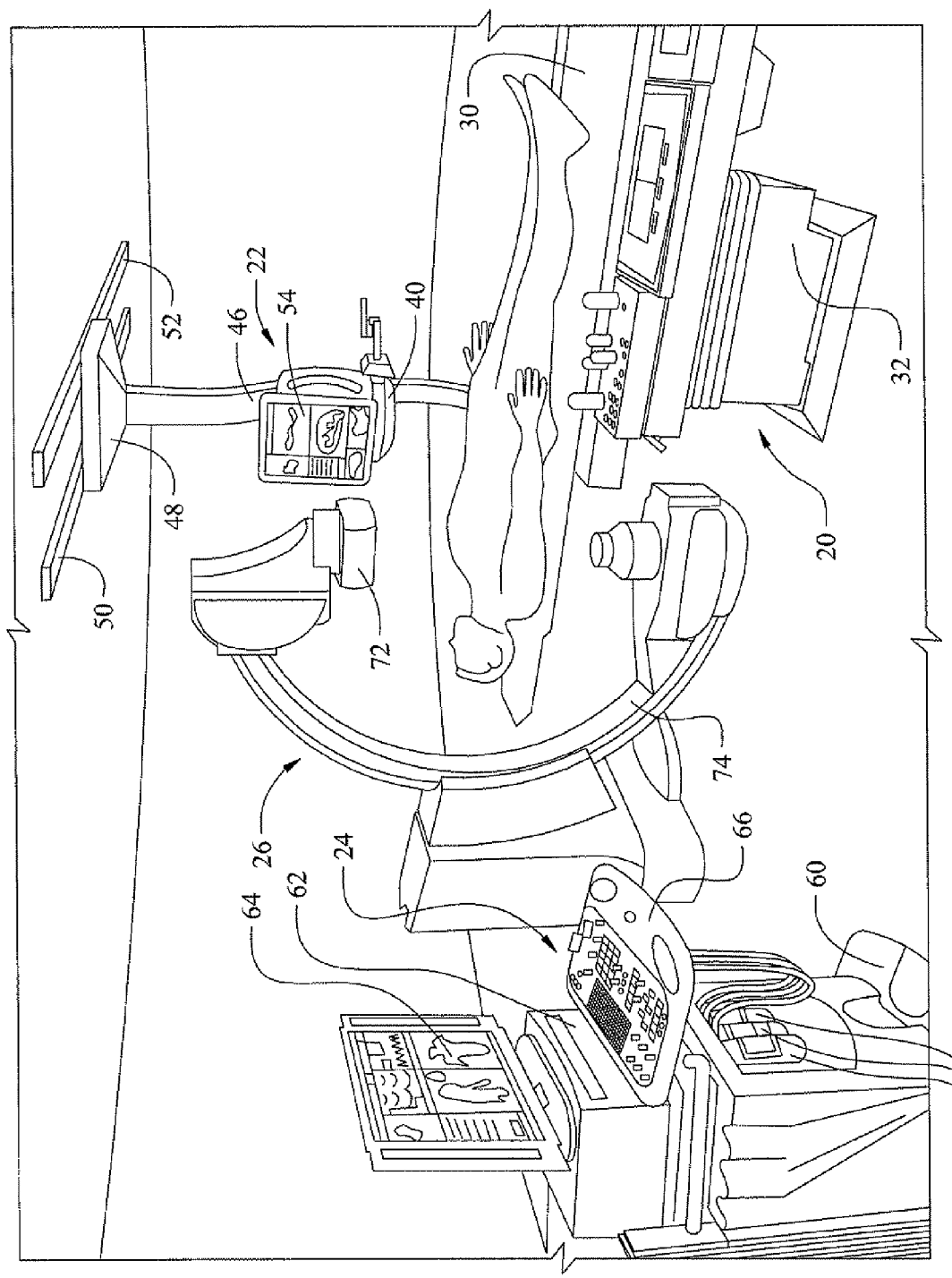
FIG. 4A is a perspective view of the procedure suite of the first embodiment, with the x-ray imaging system shown in position to image the operating region in the subject.
Figure 4B:
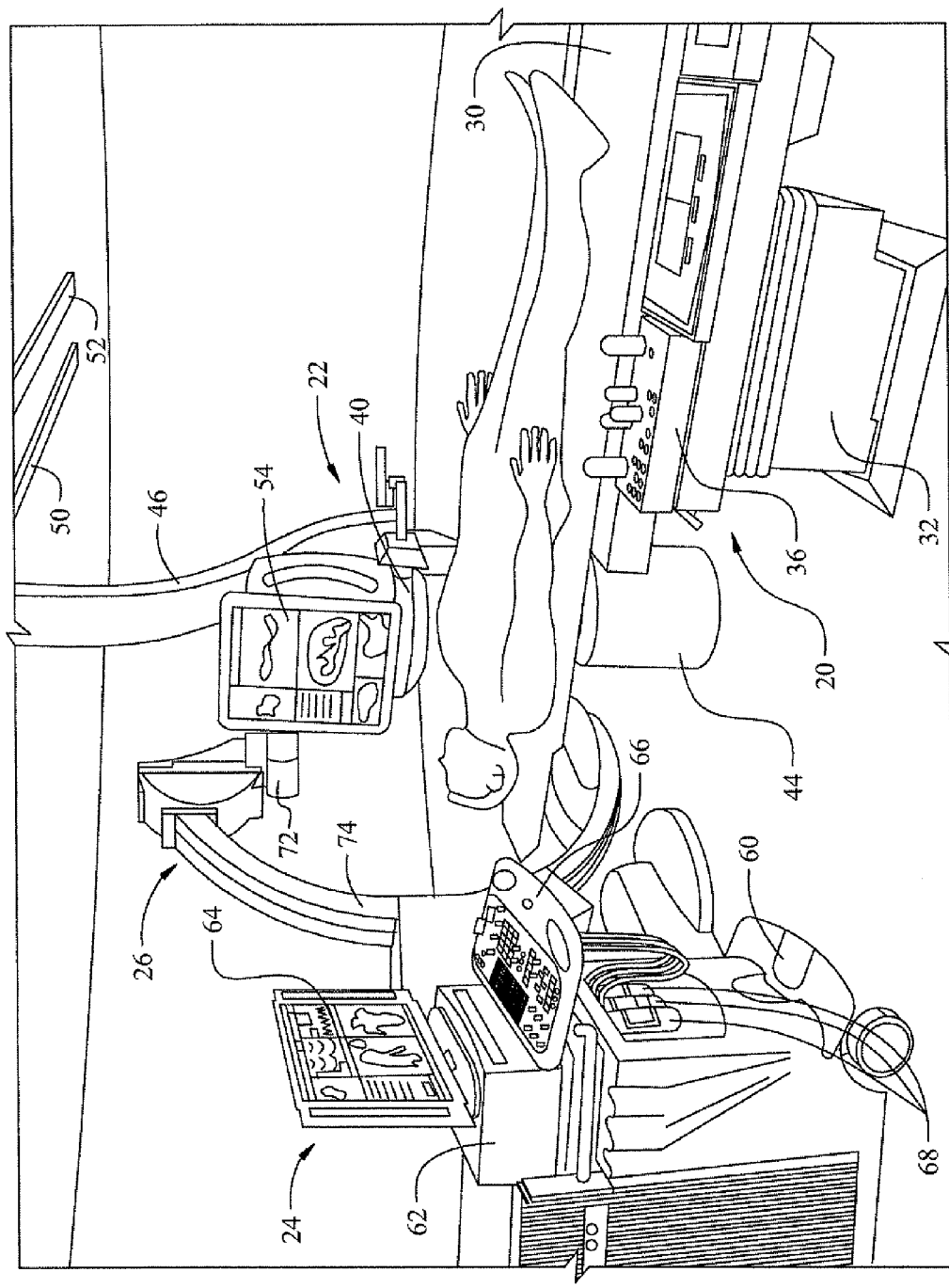
FIG. 4B is a perspective view of the procedure suite of the first embodiment, with the remote navigation system shown in position to navigate a medical device in the operating region in the subject.

The x-ray imaging system 26 is preferably a conventional x-ray imaging system comprising at least one x-ray source 70 and at least one x-ray receiver 72, mounted on a C-arm 74. The C-arm 74 is preferably a conventional C-arm that allows the C-arm to pivot about a generally horizontal axis to allow the physician or other health care professional to change the imaging angle. Other conventional movements to provide additional imaging angles can also be provided, as is known. In addition the entire C-arm 74 may pivot about a generally vertical axis to accommodate the remote navigation system 22 so that the x-ray imaging system 26 and the remote navigation system 22 can move to the subject, instead of moving the subject between the x-ray imaging and remote navigation system. (Compare FIGS. 4A and 4B). However the x-ray imaging system 26 and the remote navigation system 22 could be stationery, and the subject support 20 could move the subject between the two systems.

In accordance with one embodiment of the methods of this invention, a medical device such as an ultrasound catheter 90 having ultrasonic imaging transducer 92 (FIG. 1) thereon is introduced into the operating region, e.g., the subject's heart. (The ultrasound transducer can be forward looking, it can be side looking, or it can be a combination of forward looking and side looking.) This can be done conventionally via a puncture in the subject's femoral artery, and the distal end of the medical device is navigated to the operating region. In this preferred embodiment, where the remote navigation system 22 is a magnetic remote navigation system, the medical device also includes one or more magnetically responsive elements so that the magnetic navigation system can orient the distal end of the medical device through the application of a magnetic field.

Images from the ultrasound imaging from the distal end of the device 90 can be displayed, for example on the display 54 or the display 64. The physician or other health care professional can use the displayed image to make navigation decisions, or more preferably to control the remote navigation system to orient the distal end of the medical device. For example when navigating the medical device through a branching vessel, the device is advanced and its ultrasound images are used to detect the opening of the branch. Once the opening of the branch has been located, the remote navigation system 22 is operated to orient the distal end of the medical device toward the opening of the selected branch, so that the advancement of the device moves the device down the selected branch.

The remote navigation system 22 can be controlled using a preoperative image of the operating region, or more preferably a reconstruction of the operating region derived from preoperative imaging. By using a preoperative image or reconstruction and tracking the device length, it is possible to know (within acceptable error) the position of the distal end of the medical device relative to the preoperative image or reconstruction. The range of possible locations of the distal end can be computed and an indicator used to display the possible positions of the distal end on the preoperative image or reconstruction. This indicator can help the physician or other health care professional interpret the ultrasound images from the device. For example, when there is only one branch opening in the preoperative image or reconstruction in the vicinity of the indicator, the physician can be confident that an opening shown in the ultrasound image corresponds to the opening shown in the preoperative image or reconstruction. The physician can control the remote navigation system 22 by indicating the desired direction on the preoperative image or reconstruction, so long as the preoperative image is registered with the remote navigation system, because the ultrasound images have confirmed the location of the device in the preoperative image.

Alternatively the ultrasound image can be temporarily registered to the remote navigation system 22 by operating the navigation system to move the distal end of the medical device, and marking the direction of movement on the ultrasound image. A computer can then develop a transformation between directions on the ultrasound image and the remote navigation system, so that the physician can indicate directions to the remote navigation system directly on the ultrasonic images showing the branch opening, facilitating the navigation through the opening.

In another alternative, the ultrasound catheter images can be registered to the preoperative images as the device traverses the body lumen. Bends and openings in the body lumen provide natural landmarks, which together with rough distance information provided by tracking the length of advancement of the medical device, permit registration between these ultrasonic images and the preoperative image or reconstruction, thereby allowing the images to be used in the control of the remote navigation system.

In another alternative, the ultrasound catheter images can be registered to the preoperative images or directly to the remote navigation system 22 using magnetic localization of the distal tip of the medical device, which can provide position and orientation information of the distal tip so that the images from the distal tip can be used by the physician to control the remote navigation system.

In another alternative, the ultrasound catheter images can be registered to the preoperative images or directly to the remote navigation system using external ultrasound imaging of the operating region. An external ultrasound transducer 68 from the ultrasonic imaging unit 24 can be registered relative to the remote navigation system directly or registered to the remote navigation system via registration to the procedure suite. The external transducer 68 can have a mechanical linkage that directly tracks its position and orientation or a localization system (such as an optical localization system) can be used to determine the position and orientation of the external transducer. The external transducer 68 can then be used to locate the position and orientation of a medical device in the operating region in the subject. Once the position and orientation of the medical device relative to the external transducer 68 and the position and orientation of the external transducer 68 relative to the remote navigation system are known, the images from the ultrasound catheter can be used to operate the remote navigation system 22.

In still another alternative the x-ray imaging system 26 can be used to assist manual navigation of the medical device to the procedure site. Once at the procedure site, the x-ray imaging system can be utilized to localize the distal end of the medical device relative to anatomical landmarks or specially placed fiducial markers (which facilitate registration of the medical device with the preoperative image, and thus the remote navigation system). The x-ray imaging system 26 may already be registered with the remote navigation system 22, and thus when the x-ray imaging system is used to localize the distal tip of the medical device, the tip is also localized in the frame of reference of the remote navigation system.

In still another alternative, a preoperative image is made. This image is preferably an MR image, but could alternatively be a CT image, or multiplane x-ray image, or other image. The preoperative image may be processed to make a three dimensional reconstruction of the body lumen. Through further image processing a reconstruction of the internal surface of the body lumen can be made. Then ultrasound images of the interior of the lumen from the ultrasound catheter can then be compared with the reconstructed image of the interior of the lumen to find the best fit and thereby determine the location and orientation of the medical device. The extended length of the medical device and the preoperative model can be used to predict a range of possible locations, thereby simplifying the comparison, which need only be done over this range. Through any of a variety of methods, including, for example one or more cost functions, the best match between the actual image of the interior of the lumen made by the ultrasound catheter and the reconstruction of the lumen from preoperative imaging can be made to localize the medical device. With the ultrasound catheter thus localized, the images from the ultrasound catheter can be registered to the remote navigation system and used to control the remote navigation system. Depending on the registration, directions indicated on the image can indicate directions to the remote navigation system and/or locations on the image can indicate particular locations to the remote navigation system.

In one preferred embodiment, the Ultrasound image obtained from an Ultrasound imaging catheter is aligned with the remote navigation system as follows. The remote navigation system is integrated with an X-ray imaging system. The distal portion of the Ultrasound imaging catheter is marked as two points in a pair of X-ray images corresponding to two X-ray views. Additionally, a third point is marked in the pair of X-ray views that could be either an anatomical feature or the tip of a second device (such as a remotely operated ablation catheter, for example). This third point is also visible within the display of the ultrasound catheter imaging system. The remote navigation system display includes a pane corresponding to the ultrasound imaging plane, displayed as a circle. The approximate orientation of the selected third point within this plane, as seen on the ultrasound catheter image, is marked on this circle by the user. Since an ordered set of 3 non-collinear points suffice to uniquely determine a spatial orientation in three dimensions, a rotation matrix (approximately) relating the Cartesian frame of the remote navigation system to that of the ultrasound catheter image display plane can thereby be determined, in effect aligning the two systems. This alignment information can be used for intuitive user control of the remotely navigated medical device.

For example, as illustrated in FIGS. 15 and 16A-16C, a three dimensional wand or stylus can be used to intuitively control the orientation of the medical device. Thus, with reference to the plane of the ultrasound catheter imaging display, inward-outward (i.e., towards the user or away from the user) movements of the wand can be made to correspond to substantially into-plane or out-of-plane movements of the medical device, while lateral movement of the stylus would correspond to appropriately coordinated lateral movements of the remotely controlled medical device as seen on the ultrasound catheter imaging display.

Figure 17:
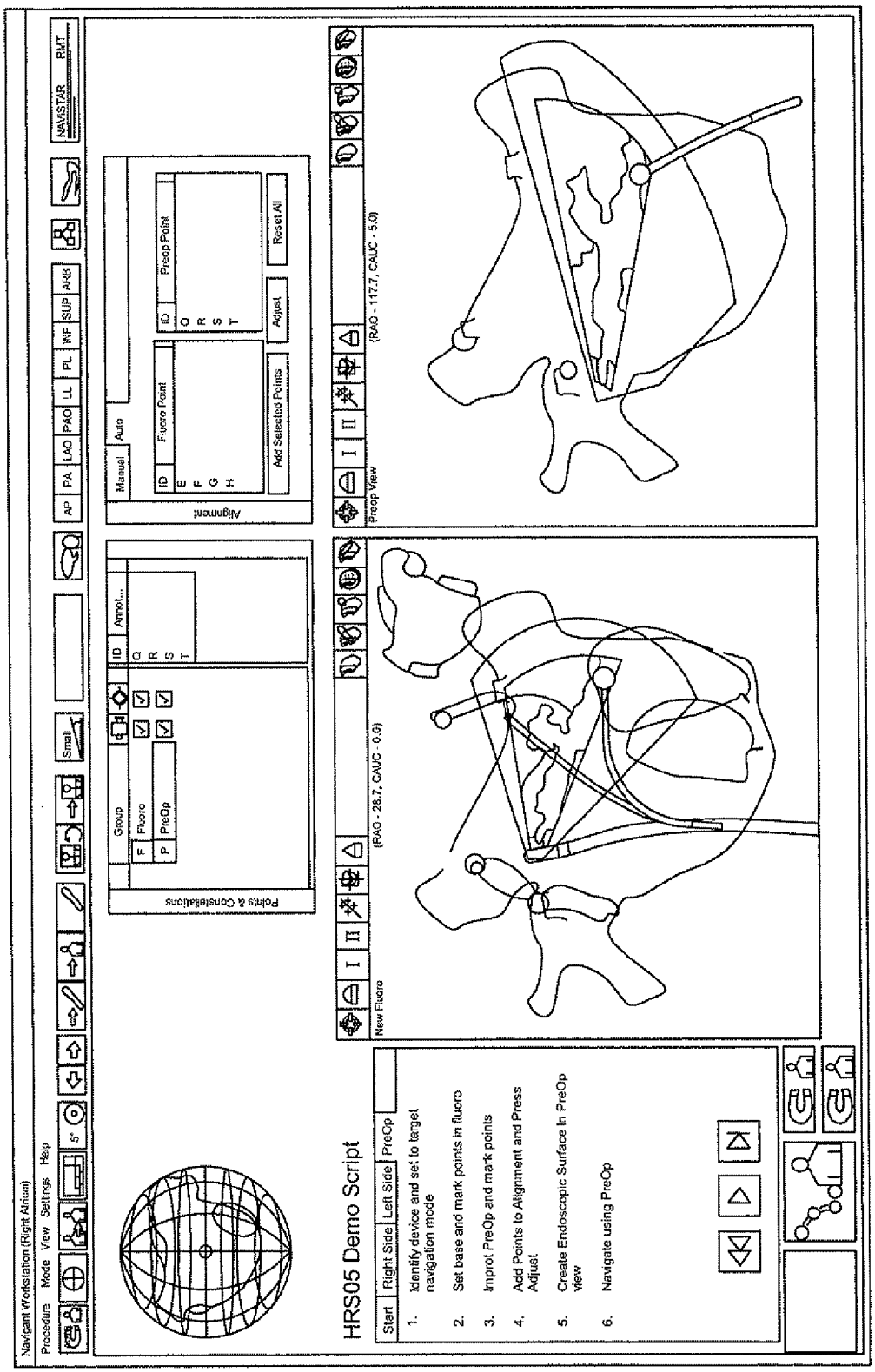
FIG. 17 is a diagram of a possible user interface screen, illustrating the possible fusion of ultrasound imaging with the displays for operating the remote navigation system.

In another preferred embodiment illustrated in FIG. 17, the ultrasound catheter and remote navigation systems are integrated. In particular, the ultrasound catheter image is integrated into the display of the remote navigation system. The above steps can be repeated, except that now the actual location of the third point (anatomical feature or tip of second medical device) is marked directly on the ultrasound image in the display of the remote navigation system. This provides sufficient information to effect a registration of the Cartesian frame of the remote navigation system with that of the ultrasound catheter image. Further, the ultrasound image (plane) can now be displayed in fused fashion with either an intraoperatively acquired x-ray image or with a pre-operatively acquired 3D image (such as a CT or MR scan). Desired anatomical target points to which it is desired to navigate the medical device can be marked directly in the fused image plane, or elsewhere either in the X-ray image or 3D image using the ultrasound image plane as a visual reference.

In another preferred embodiment, the ultrasound catheter and remote navigation systems are integrated. Three dimensional (pre-operative) image data on the remote navigation system is fused with the ultrasound catheter image data on the display of the remote navigation system. The transparency of the 3D pre-operative image data is suitably adjusted so that it adds extra detail to the ultrasound catheter image. In this manner, the ultrasound image is placed in anatomical context. Details that may be incompletely seen or not visible in the ultrasound image by itself now provide a context in the fused image so that a remotely navigated medical device can be suitably steered.

Figure 18:
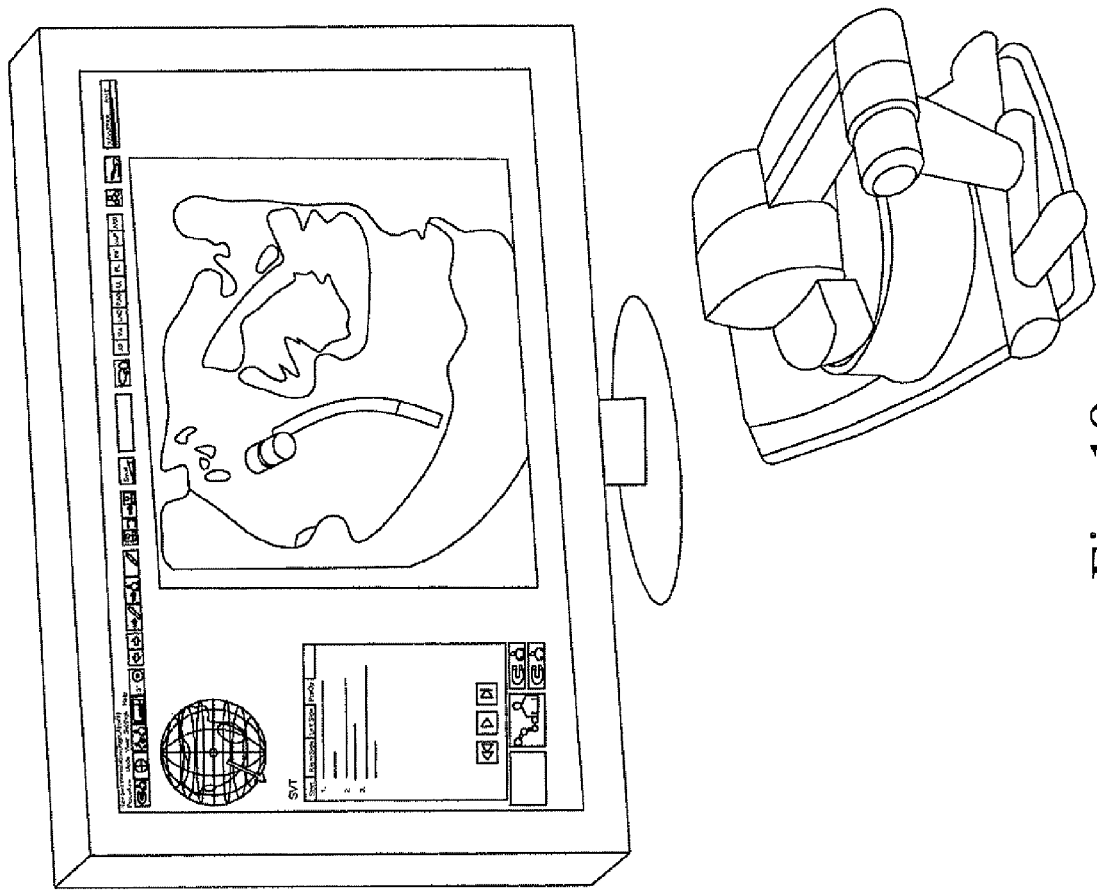
FIG. 18 is a diagram of another possible interface screen illustrating the possible fusion of 3-D ultrasound imaging with the displays for operating the remote navigation system.
Figure 19:
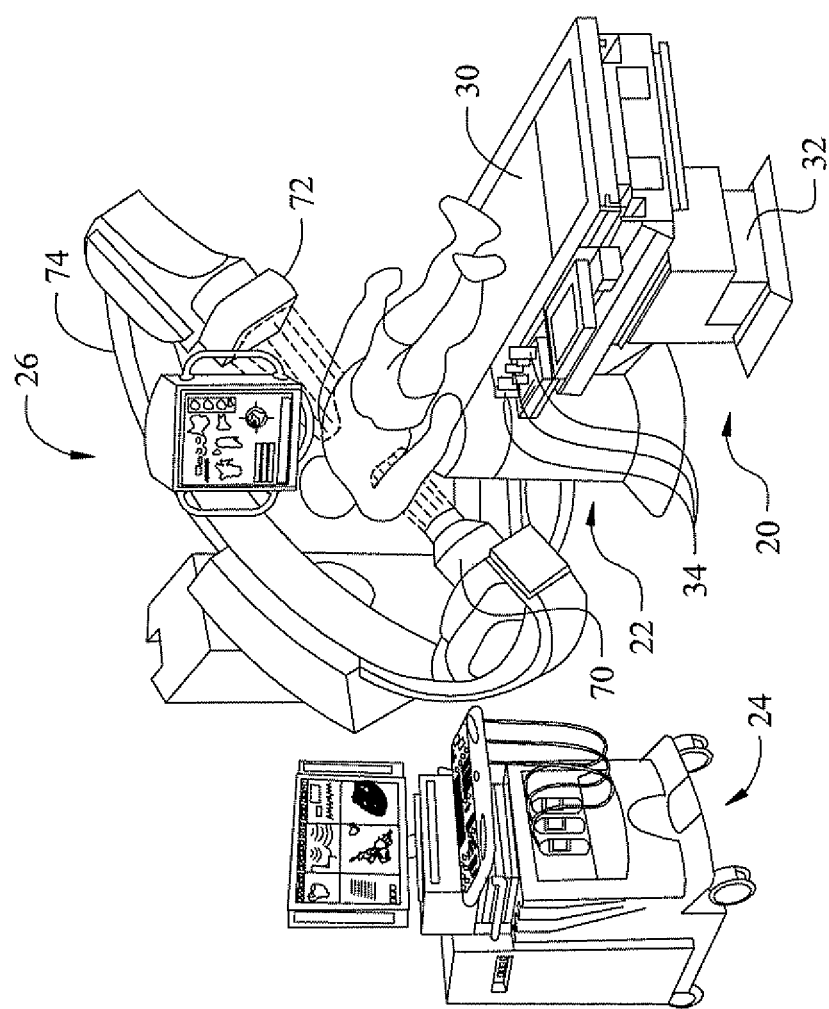
FIG. 19 is a perspective view of a procedure suite, showing an arrangement which allows a movable remote navigation system to be positioned to allow fluoroscopic imaging.
Figure 20:
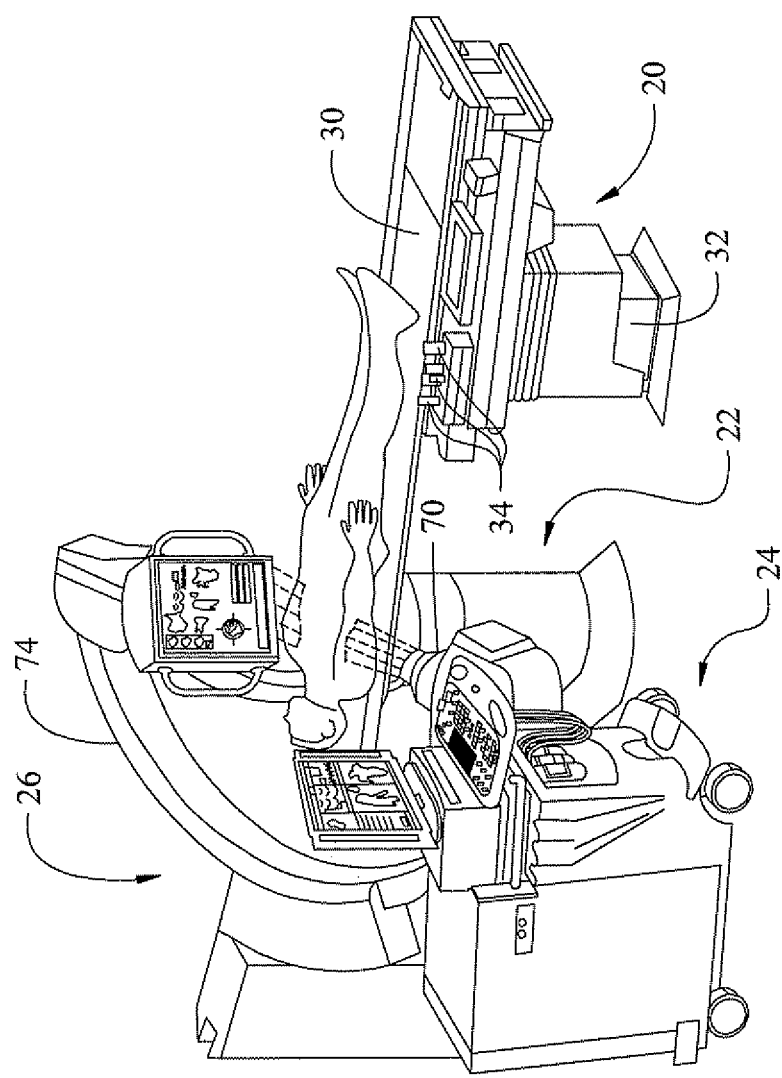
FIG. 20 is a perspective view of the procedure suite shown in FIG. 19 from a different view point.
Figure 21:
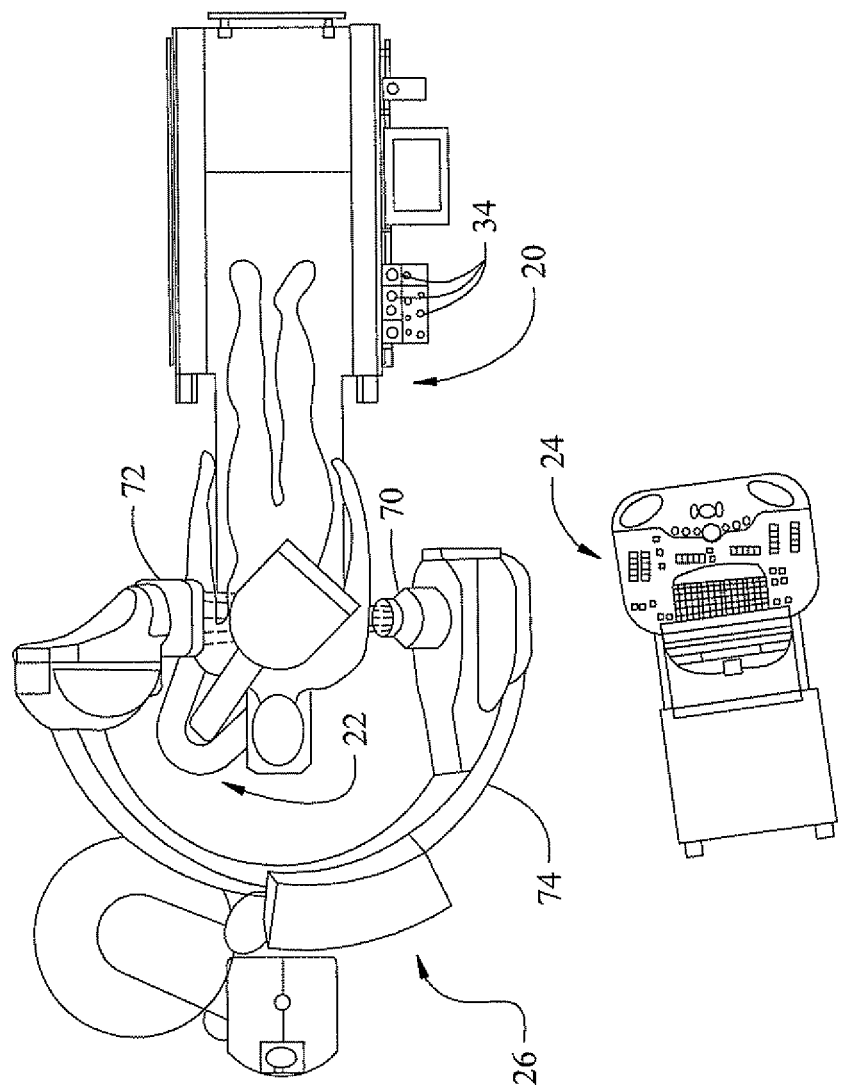
FIG. 21 is a top plan view of the procedure suite shown in FIG. 19.

In still another preferred embodiment, illustrated in FIG. 18, the ultrasound catheter imaging system is integrated with the remote navigation system. The Ultrasound catheter is used to image (among others) a remotely navigated medical device. In general, the remotely navigated device could move outside the imaging plane of the Ultrasound catheter. In this case, the movements of the remotely navigated medical device can be tracked, either by image processing of the ultrasound image or by monitoring applied control variables of the remote navigation system. The orientation of the Ultrasound catheter is then modified suitably, either by robotic means or manual means, such that the remotely navigated catheter is always well-centered within the observed Ultrasound field of view. In the latter case, the remote navigation system displays a message indicating to the user whether the Ultrasound catheter should be torqued clockwise or counterclockwise. Alternatively, depending on the current viewing orientation of the Ultrasound catheter, the remotely navigated medical device can be moved into its field of view by applying a suitable control variable. Subsequently the medical device and the Ultrasound catheter viewing orientation can be moved in corresponding fashion such that the remotely navigated medical device always stays within the field of view of the Ultrasound catheter.

The ultrasound imaging catheter in general produces image data within a limited spatial region in the form of a wedge-like image plane, corresponding to an ultrasound beam that fans out from a thin arrangement of transducers located length-wise along a distal section of the imaging catheter. Due to the thin-plane form of the imaging/visible region, a device that is located within this image can easily move out of the imaging region as the device is steered within the anatomy. In one preferred embodiment of coordinated movement of imaging catheter and remotely navigated device, the imaging catheter and remotely navigated device are independently controlled by two advancer/rotation mechanisms that can either advance or retract, or axially rotate the respective device, or both. In a preferred embodiment either one or both of these advancer/rotation mechanisms can be directly computer-controlled. In this case, the computer could automatically process image data from the imaging catheter, detect the remotely navigated device in the image, track the latter's motion as it moves to check if it is moving out of the field of view, determine a rotation and/or advancement/retraction of the imaging catheter, and then suitably advance/retract or rotate the imaging catheter to bring the remotely navigated device back into the field of view of the imaging catheter.

In another preferred embodiment, the navigation control variables that are applied to steer the remotely navigated device can be used to determine an appropriate tracking motion of the imaging catheter. To illustrate this, consider the case where the remote navigation system is a magnetic navigation system that steers a remotely navigated magnetic catheter. Let an initial magnetic field be applied in a direction $v_1$, and let us assume that the magnetic catheter is well within the field of view of the imaging catheter. Let the image plane of the imaging catheter be described by a normal vector $n_1$ (perpendicular to the long-axis of the catheter in a right-handed sense). Let the long axis of the imaging catheter be described by the unit vector a. We can distinguish two cases, one where the orientation u of the base of the catheter (at the pivot or support of the catheter) is known, and the other where u is not known. Let $v_2$ be a new applied magnetic field direction. First we consider the case where u is known. If the catheter is free to move, it will consequently reorient such that the new plane of the catheter is described by the unit normal $y=y'/|y'|$, where $y'=u \times v_2$. The normal $n_2$ to the best viewing plane for the imaging catheter is then found such that the quantity $C=(n_2 \cdot y)$ is maximized. Thus, the imaging catheter is rotated about its axis a by an angle $\phi$ such that $n_2=R_a(\phi)n_1$ maximizes C, where $R_a(\phi)$ is a 3×3 rotation matrix defining a rotation by an angle $\phi$ about a.

In the case where the catheter base orientation u is not known, we guess that the new field direction $v_2$ lies in the plane of the catheter. In this case we pick a new normal direction $n_2$ to the new imaging plane of the imaging catheter such that the quantity $D=(n_2 \cdot v_2)$ is minimized. Thus, the imaging catheter is rotated about its axis a by an angle $\phi$ such that $n_2=R_a(\phi)n_1$ minimizes D, where $R_a(\phi)$ is a 3×3 rotation matrix defining a rotation by an angle $\phi$ about a.

Even in the case where u is known, it may in some cases be advantageous to pick a new imaging catheter imaging plane (defined by $n_2$) such that a weighted combination of the above cost functions C and U is minimized; for instance we can pick an optimal rotation angle that minimizes $(w_1 D - w_2 C)$, where $w_1$ and $w_2$ are suitable weights.

In a similar manner, when the medical device is steered by the remote navigation system in such a manner that it is no longer easily visible in the imaging plane of the ultrasound imaging catheter, the ultrasound imaging catheter can be manipulated or re-positioned by a robotic mechanism that applies one of three movements: (i) an advancement, (ii) a retraction or (iii) a re-orientation. For example, the ultrasound imaging catheter can pass through a sleeve or collar (driven by a drive mechanism) that engages and grips the imaging catheter and rotates it about its long axis to re-orient it; alternatively or in addition, the shaft of the imaging catheter can pass between drive wheels (driven by a suitable drive mechanism) that grip the shaft and can turn to advance or retract the imaging catheter. Such drive mechanisms can be computer-controlled and can be suitably designed by one skilled in the art of mechanisms. The appropriate movement to be applied may be determined, for example, analogously to the above-described optimization method in the case of a magnetic remote navigation system, or by similar methods in the case where other remote navigation technologies are employed. The specific computations described here are given for illustrative purposes only and those skilled in the art can extend these results to any of a variety of remote navigation technologies. Accordingly, the scope of the specific embodiments of the invention are limited only by the appended claims.

In an alternate preferred embodiment the advancement/retraction or rotation movements of at least one of the devices can be controlled by a user via an input interface such as a push-button or a joystick. Thus, for example, the user can watch the image generated by the imaging catheter as the remotely navigated device is steered within an anatomical region and decide to retract or rotate the imaging catheter such that the remotely navigated device remains within the field of view. For example, the imaging catheter can be advanced or retracted by a catheter advancer system suitably to maintain the medical device within its field of view. An example of a catheter advancer system is described in U.S. Pat. No. 7,276,044; U.S. patent application Ser. No. 11/770,639, Published as 20080045892; U.S. patent application Ser. No. 11/634,388, Published as 20070149946, the disclosures of which are incorporated herein by reference. A catheter advancer system that can also rotate the device is described in pending U.S. patent application Ser. No. 10/858,485, Published as 20060041245, the disclosure of which is incorporated herein by reference.

Upon registration of the medical device with the remote navigation system 22 as described above, the device can be navigated using only the ultrasound images from the medical device, without any external real time imaging of the operating region. The preoperative image or reconstruction can also be displayed, with an indicator of possible position (based on extended device length) or actual position (based upon comparison between the device imaging and the preoperative imaging or other localization) to help orient the physician in the anatomy. Real-time ultrasonic imaging from the ultrasonic imaging system 24 can also be used to display an image of the device in the operating region to help orient the physician. However continual x-ray imaging, while helpful, is not necessary to successful navigation.

In the preferred embodiment of the procedure suite the subject support 20 and the navigation system 22 are constructed so that at least one of the support 20 and the navigation system 22 is movable to change the location of the operating point of the navigation system relative to a subject on the subject support. In a first alternate construction, only the navigation system 22 moves to change the location of the operating point in the subject. In a second alternative construction, only the subject support 20 moves to change the location of the operating point in the subject. In a third alternative construction, both the navigation system and the subject support move to change the location of the operating point in the subject. By changing the location of the operating point in the subject, and in particular by keeping the operating point close to the current location of the magnetically responsive medical device, the magnets in the magnet units 40 and 42 can be made smaller and lighter, and still create a magnetic field in a desired direction of sufficient strength to orient the distal end of the device.

Device localization can be used to track the current position of the distal end of the medical device, and a control can automatically move at least one of the subject support 20 or the remote navigation system 22 to automatically maintain the operating point of the remote navigation system in the vicinity of the distal end of the device. Magnetic localization systems, image processing systems, or any other system for effectively locating the distal end of the device can be used.

Figure 13:
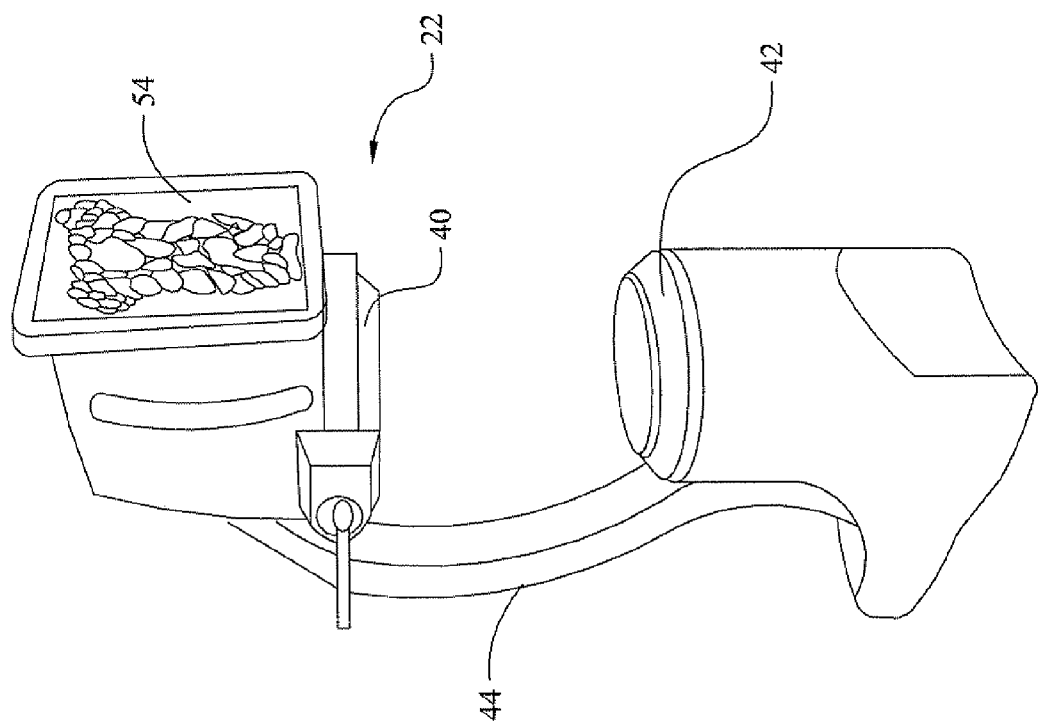
FIG. 13 is perspective view of an integrated remote navigation system and display useful in the various embodiments of the invention.

As shown best in FIG. 13, the remote navigation system 22 can also be mounted on the floor, rather than being suspended from the ceiling.

In another preferred embodiment, the ultrasound catheter provides a 3D reconstruction of the anatomy of interest that could include a remotely navigated medical device. The 3D image is displayed in cut-away or endoscopic form such that the device is clearly visible and is registered with the remote navigation system as described above. A 3D wand or stylus device, possibly incorporating haptic feedback, is used to control the movements of the remotely navigated medical device in intuitive fashion. Thus, since the ultrasound catheter and remote navigation systems have been registered or aligned, movements of the wand can be directly converted to suitable changes of control variables such that the medical device moves in spatial concordance with the movements of the wand.

Figure 14:
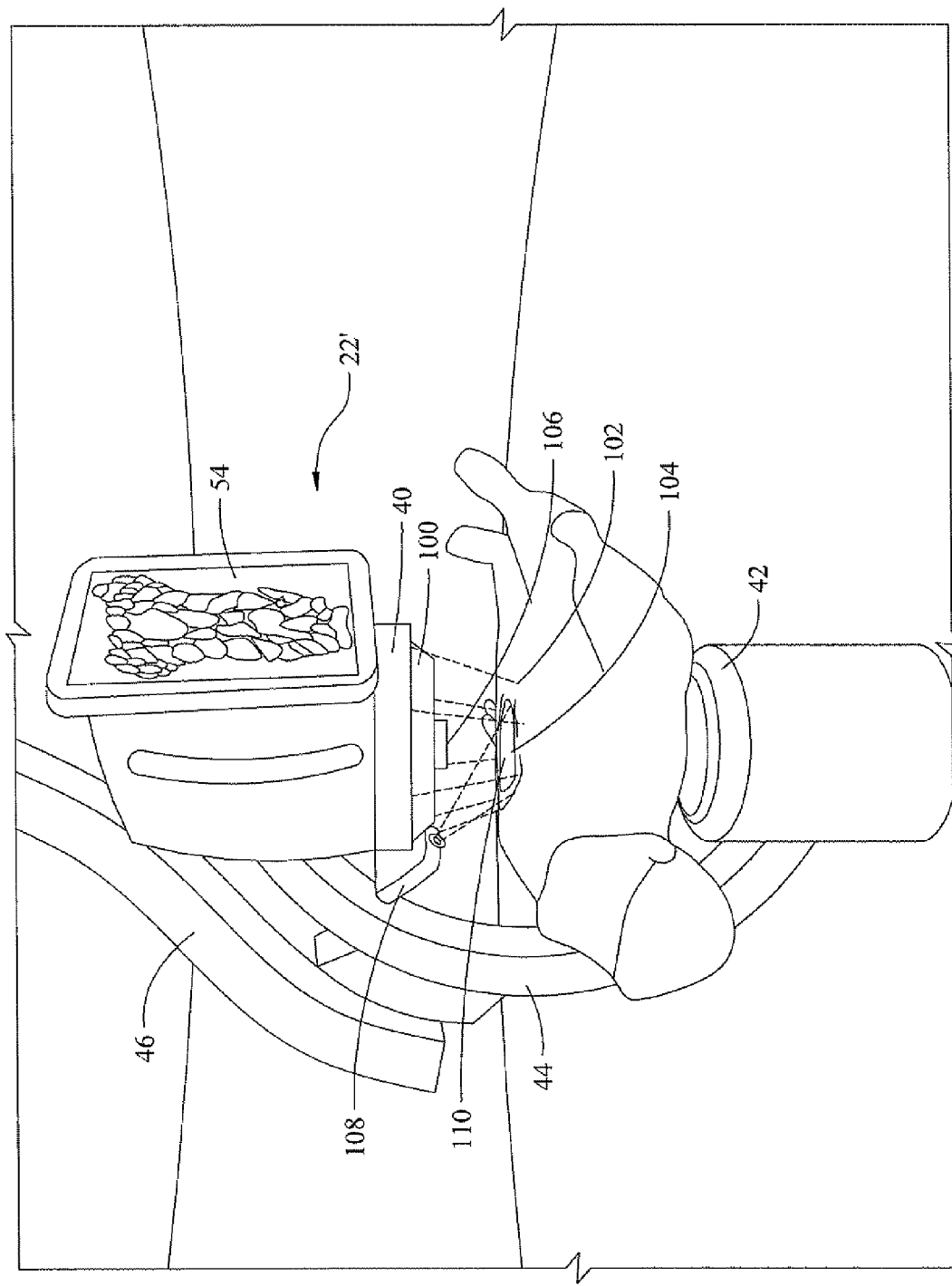
FIG. 14 is a perspective view of an integrated remote navigation system incorporating a projection system for projecting information onto a subject on the subject support.
Figure 15:
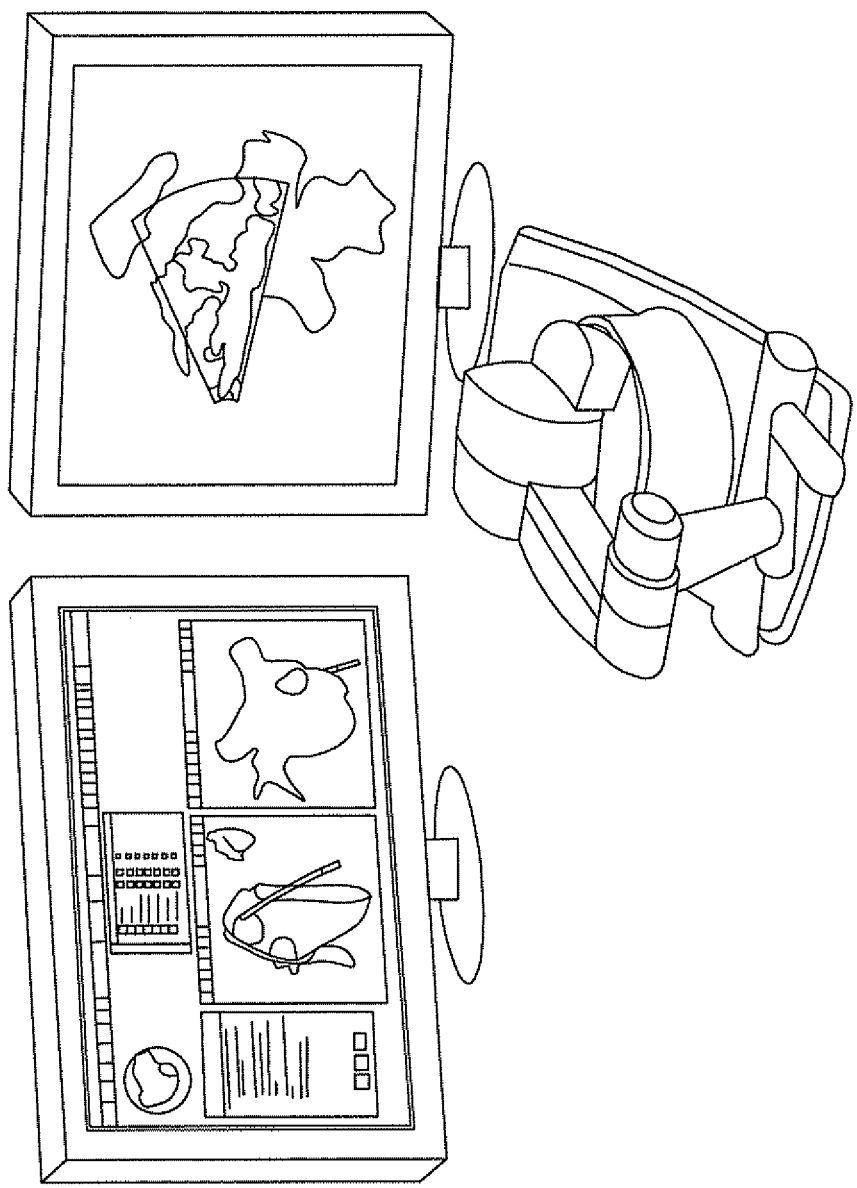
FIG. 15 is a schematic diagram of a user interface for controlling a remote navigation system in accordance with some preferred embodiments of this invention, showing a computer interface screen side by side with an ultrasound imaging screen and a coordinated input wand for operating the remote navigation system.
Figure 16:
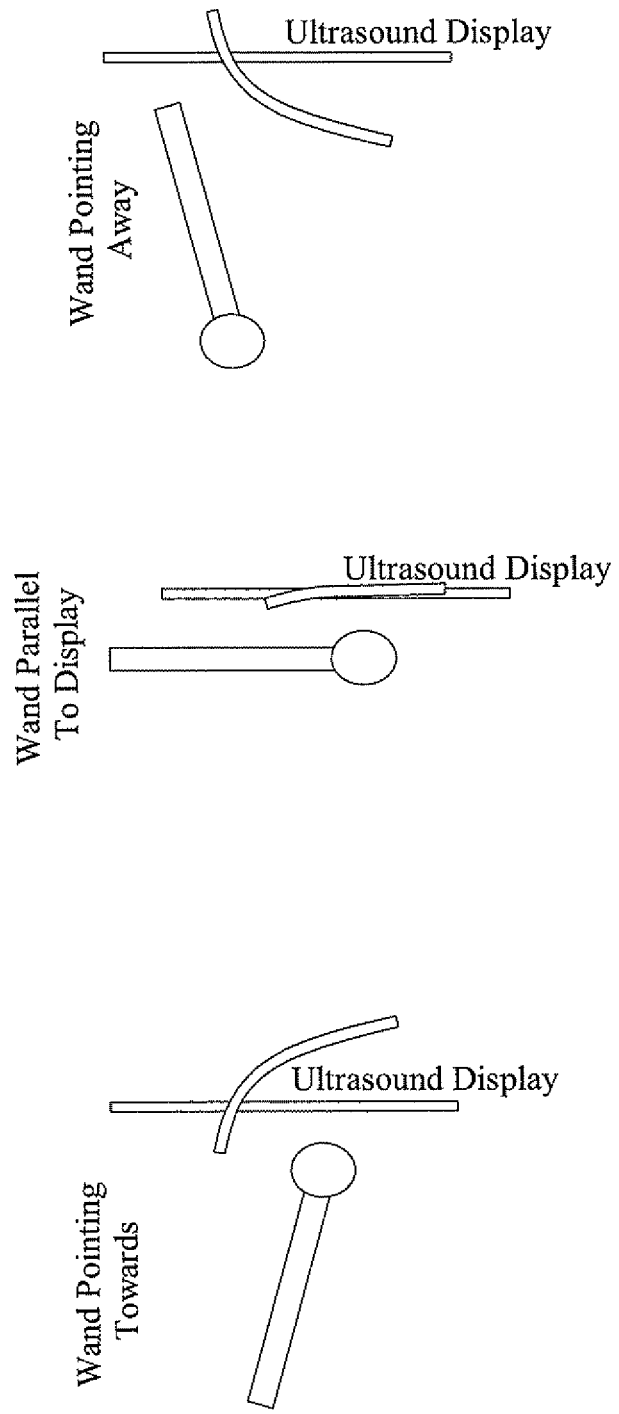
FIGS. 16A-16C are schematic diagrams showing one possible implementation of a remote control for a remote navigation system.

As shown in FIG. 14, in a third embodiment of this invention, an alternate embodiment of a remote navigation system 22' includes at least one projector 100 that projects an indicator 102 of the location of the operating point onto the surface of a subject on the subject support. In first construction, the indicator 102 indicates an axis between the magnet units on which the operating point lies. In a second construction, the indicator 102 is a ring 104 surrounding an axis between the magnet units on which the operating point lies. This ring can be made of a plurality of discrete markers, or can be a continuous ring. The indicators help the physician position the operating point in the subject.

The system 22' preferably also comprises a camera 106 for making an image of the surface of subject on the subject support 20, which image can be displayed on the monitor 54. The camera can also capture the image of the indicator for indicating the location of the operating point, so that the physician can see the location of the operating point relative to the subject on the monitor. The monitor 54 can be part of a control interface, on which the physician can indicate the desired location of the operating point on the displayed image of the subject, and at least one of the subject support 20 or remote navigation system 22 moves relative to bring the operating point to the selected location relative to the subject.

The system 22' preferably also includes a projector 108 for projecting an image 110 onto the surface of the subject on the subject support 20. This image 110 may be a preoperative or live image of the operating region, an image of idealized anatomy; actual or reconstructed image of the medial device being navigated inside the body, information about the status of the navigation system, information about subject's status, etc. This projection may be viewed directly by a physician observing the subject. Alternatively, this projection may be viewed on the monitor which picks up the projection as part of the image of the subject. This allows the physician to better understand the spatial and directional relationships of the subject anatomy and the position and orientation of the medical device.

The projection 110 on the subject is preferably one that helps the physician orient the medical device in the subject's anatomy, and therefore can include a preoperative image of the operating region, and an image of idealized anatomy of the operating region, or a current image of the operating anatomy from any available imaging source including x-ray or fluoroscopic imaging or ultrasound imaging. If a real time image of the operating region is used, the medical device is preferably designed so that it is visible in the projected image. If a preoperative image or an image of idealized anatomy is used, then a representation of the medical device can be superimposed or otherwise combined with the image. For example in the case of the magnetically guided medical device knowledge of the applied magnetic field and device length can be used to predict the location of the distal tip and the configuration of the distal end portion. Similarly with other navigation systems, knowledge of the applied control variables often makes it possible to predict the location of the distal tip and the configuration of the end portion. Alternatively device localization or image processing may make it possible to superimpose an image of the device onto the preoperative or idealized image, to help the physician visualize the procedure. This composite is than projected on the subject so that the physician can visualize the operating region and see the orientation of the medical devices.

In each of the preferred embodiments, the entire suite is preferably under the control of a computer (not shown) that runs interface software for taking inputs from the physician from either the controls 36 on the support, the monitor 54 or the computer 62, and translates them to instructions for the remote navigation system 22, the subject support 20 and the ultrasound and x-ray systems 24 and 26. If a localization system is used to localize either the medical device, reference catheters, or the ultrasound transducers 68, it too can be controlled by, and input data to, the computer.

In some instances it may be desirable to have a portable remote navigation system that can be moved into and out of the procedure suite, or which can be moved among a plurality of procedure suites. This allows a procedure suite to be used for procedures with and without the assistance of a remote navigation system; it allows the remote navigation system to be selectively used with an imaging system; and it allows a single remote navigation system to be shared among a plurality of procedure suites. One implementation of such a system is illustrated in FIGS. 19-26, where the procedure suite comprises a subject support 20, a remote navigation system 22 for remotely orienting the distal end of a medical device in an operating region in a subject on the subject support; and an x-ray imaging system 26 for imaging the operating region in a subject on the subject support. Additional imaging systems, such as ultrasound imaging systems like system 24 described above can be used instead of, or in conjunction with x-ray imaging system 26.

The subject support 20, as described above, comprises a bed 30, and a base 32 for movably supporting the bed. In one version of the preferred embodiment the base supports the bed for movement in three mutually perpendicular directions, e.g. axially, transversely, and vertically. This allows a physician or other health care worker to control the position of the operating point of the remote navigation system 22 relative to the subject, and preferably also allows the physician or other health care worker to move the support so that the navigation system 22 can be moved relative to the x-ray imaging system 26.

In another, preferred version of the preferred embodiment, the base 32 supports the bed 30 for rotation about a generally vertical axis so that the subject can be pivoted between the imaging system and the remote navigation system. A plurality of controls 34 can be provided adjacent the bed, so that the attending physician or other health care worker can conveniently control the procedure suite and its various components.

The remote navigation system 22 is adapted for remotely orienting the distal end of a medical device disposed in an operating region in a subject on the subject support 20. In this preferred embodiment the remote navigation system 22 is a remote magnetic navigation system, having at least first and second source magnet units 40 and 42 capable of creating a magnetic field in any direction in the operating region in the subject on the support 20. As discussed above, while the preferred embodiments is shown and described with two magnet units, the invention is not so limited, and more than two magnet units, e.g., three units spaced 120° apart or in some other configuration, or any other number or arrangement of magnet units can be used as appropriate. The magnet units 40 and 42 project a magnetic field at an operating point between them of sufficient strength to orient one or more magnetically responsive elements on the distal end of the medical device.

Figure 5:
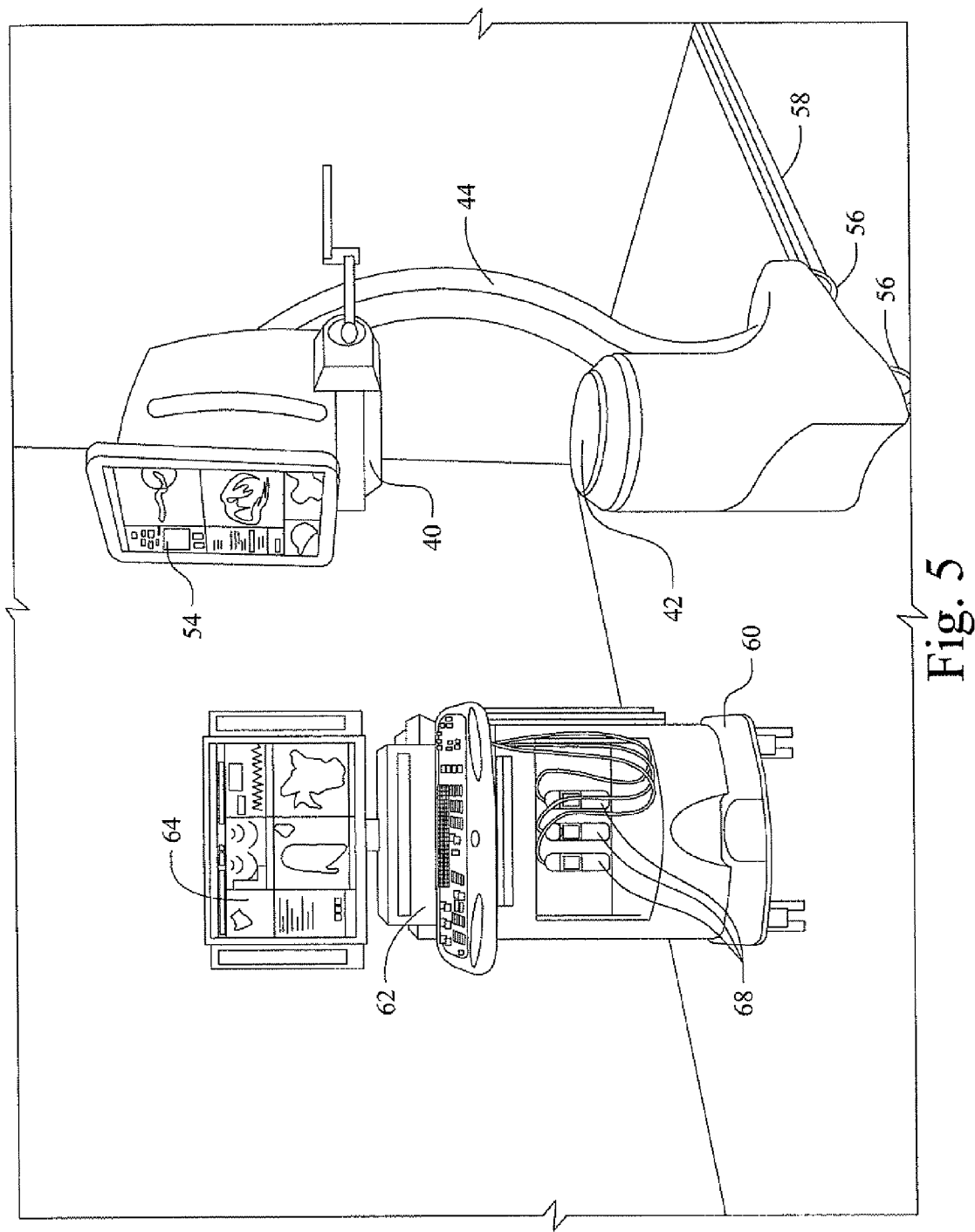
FIG. 5 is a perspective view of a procedure suite in accordance with a second preferred embodiment, including a remote navigation system and an ultrasound imaging system.
Figure 6:
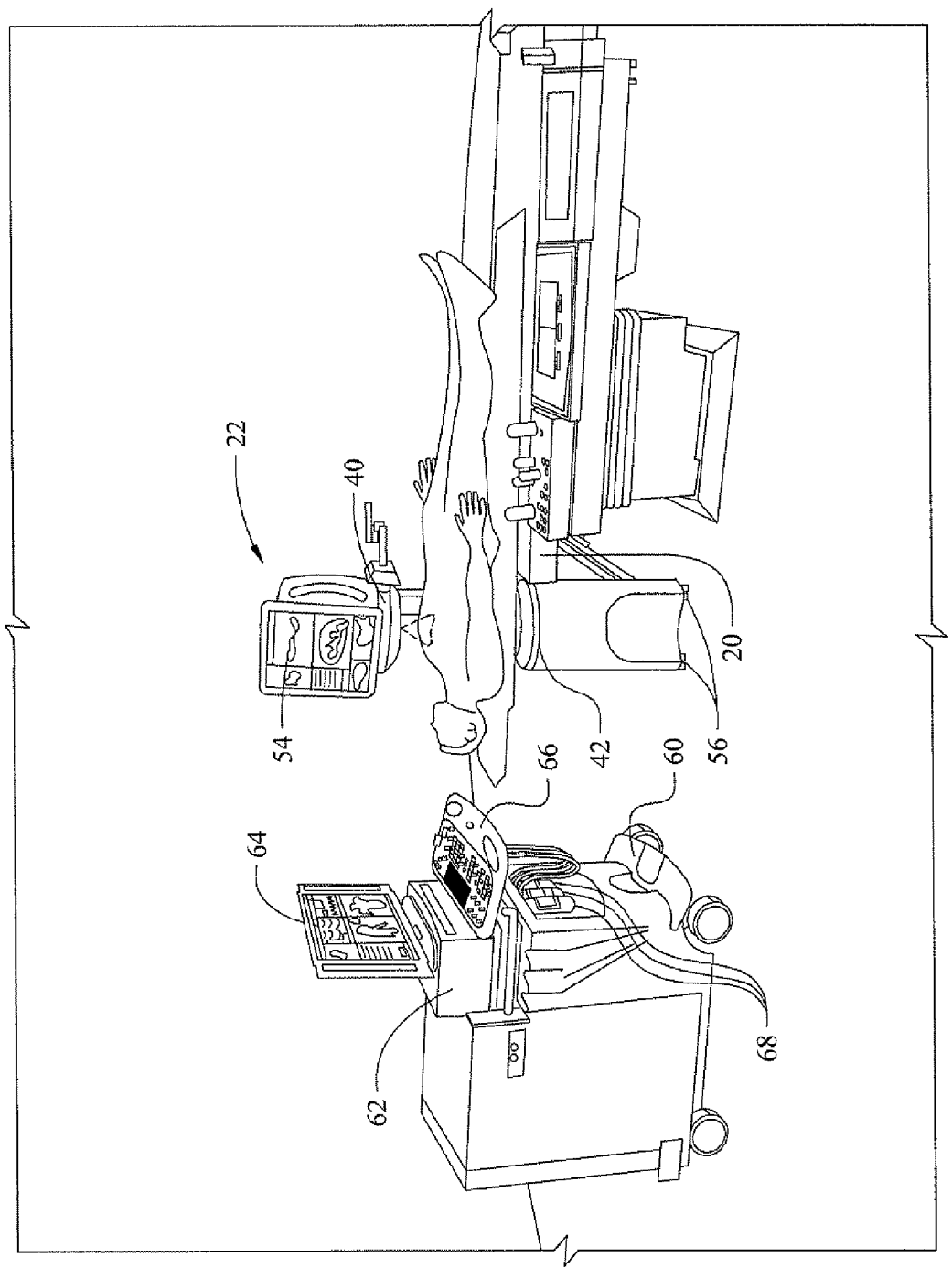
FIG. 6 is a perspective view of the procedure suite of the second preferred embodiment, showing a subject on the subject support.
Figure 7:
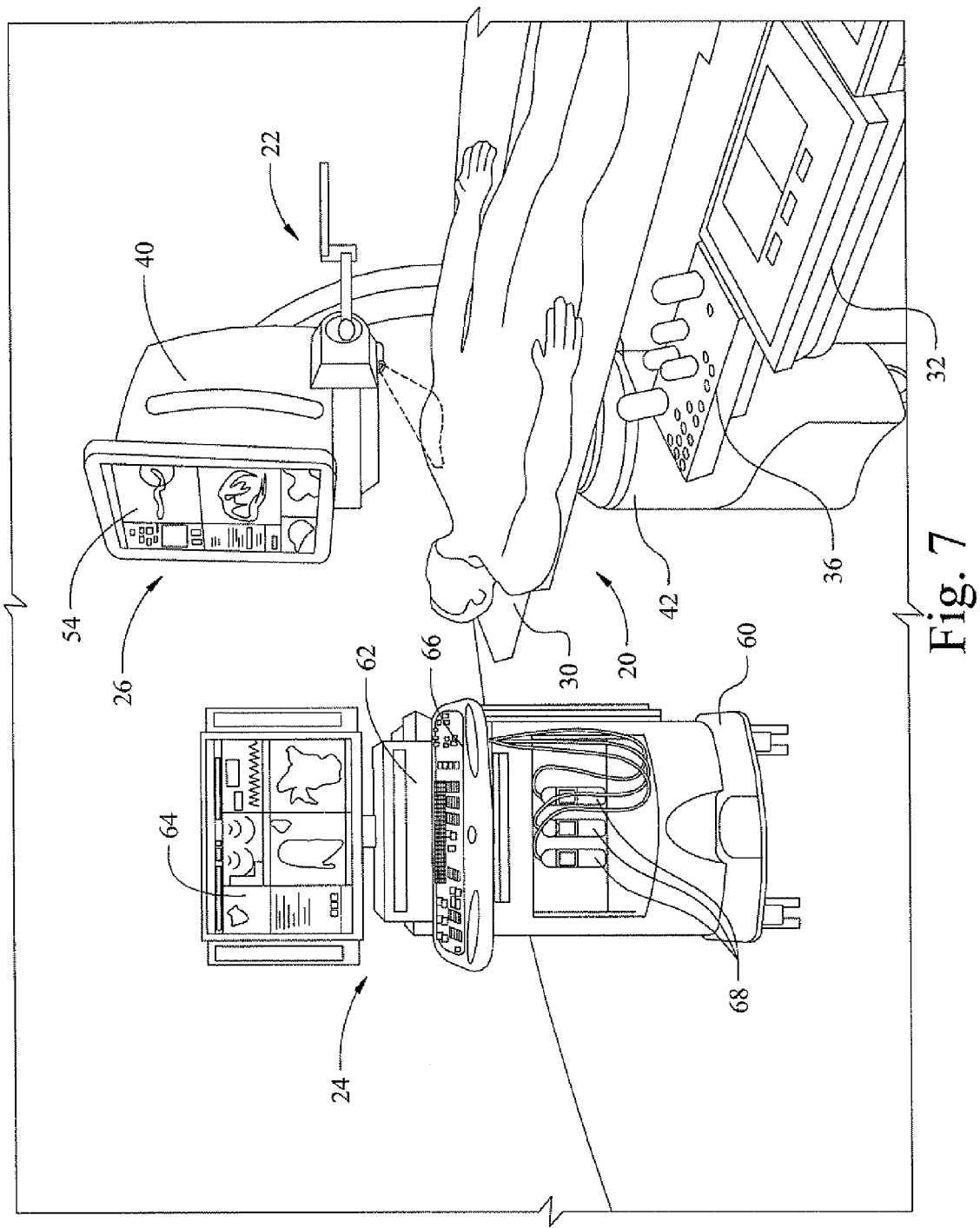
FIG. 7 is an enlarged perspective view of the procedure suite of the second preferred embodiment, from a different view point than FIG. 6.
Figure 8:
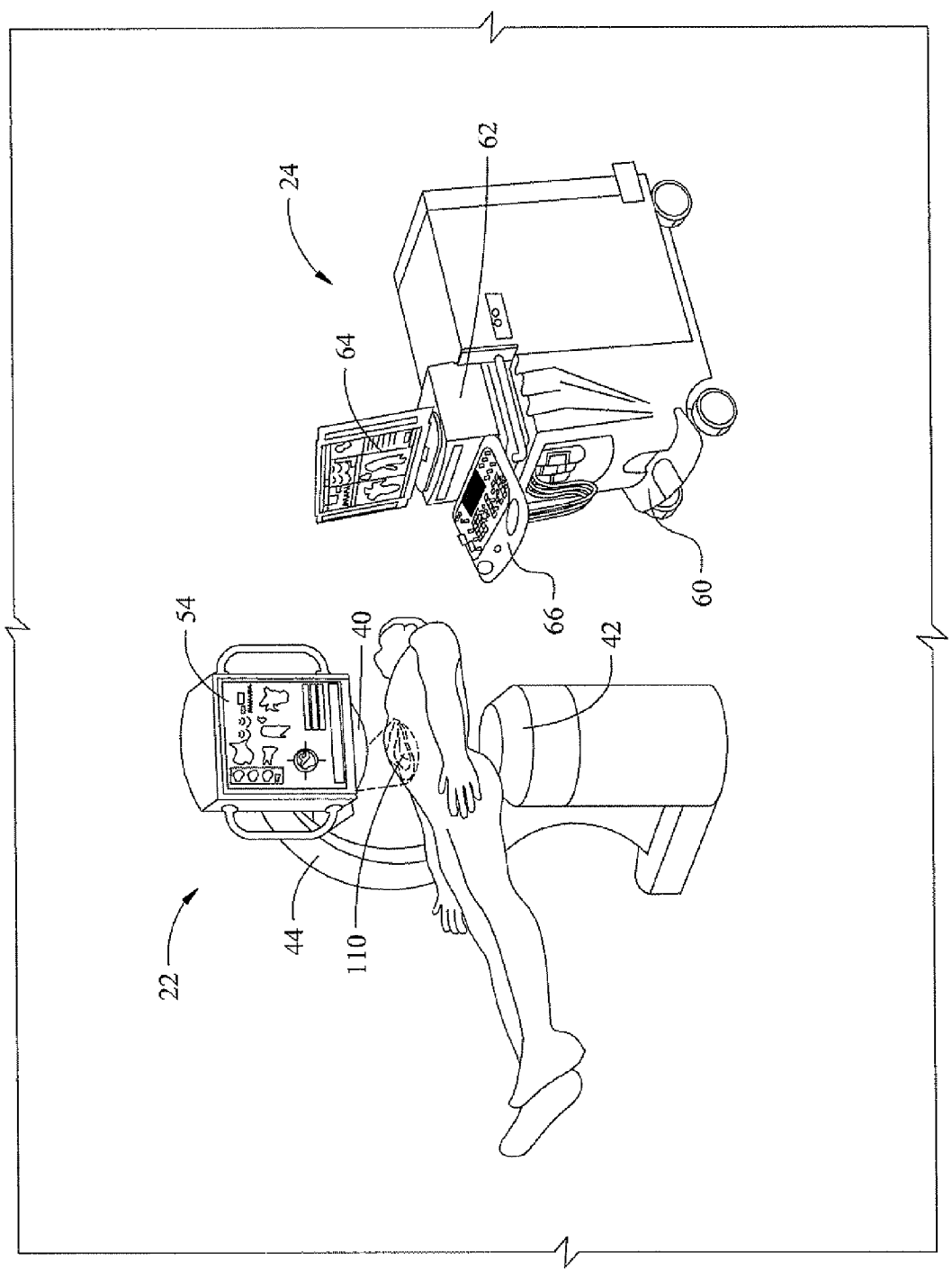
FIG. 8 is a perspective view of the procedure suite of the second preferred embodiment showing a subject, but with the subject support removed to show the other components of the suite.
Figure 9:
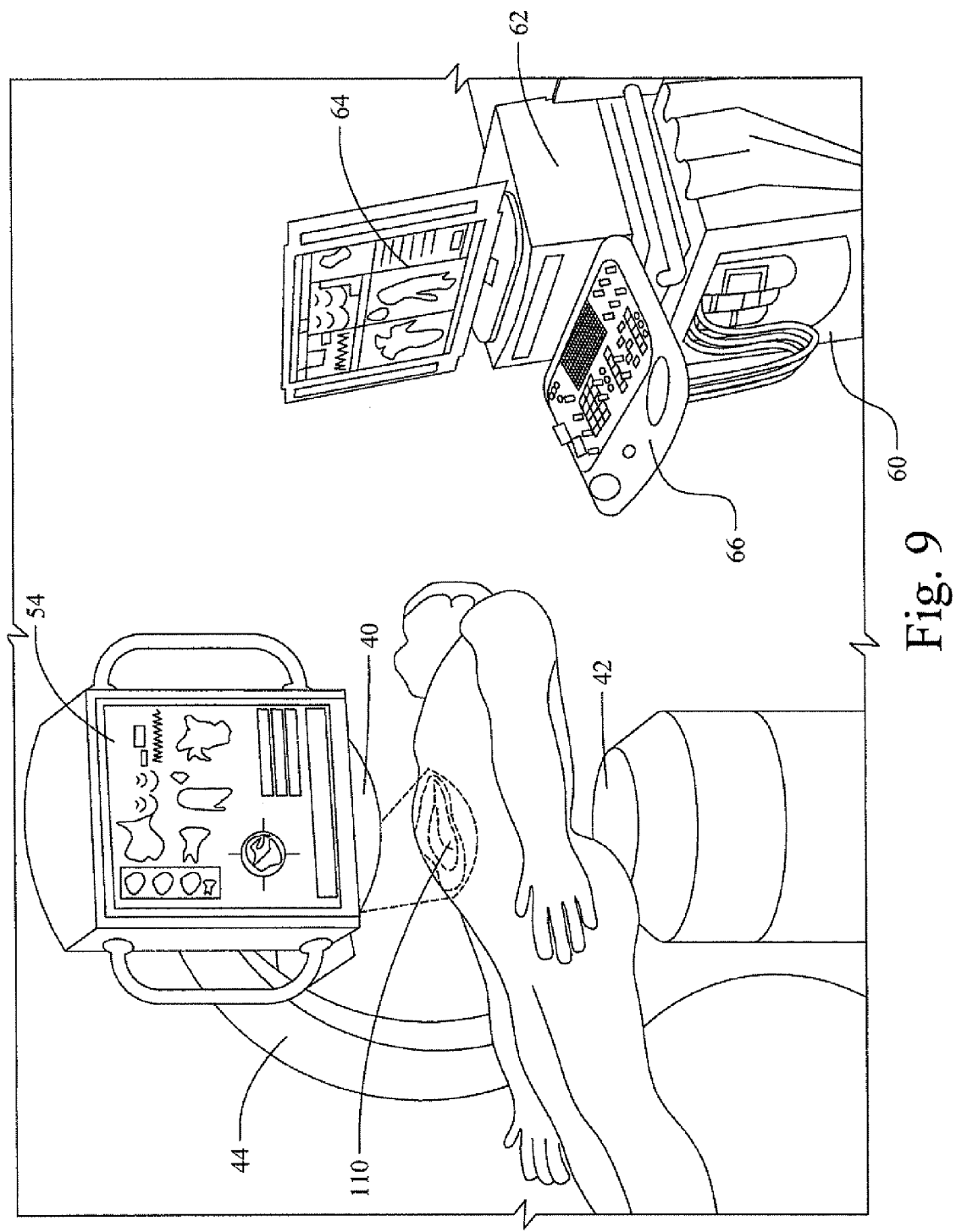
FIG. 9 is an enlarged perspective view of the procedure suite of the second preferred embodiment, from a different view point than FIG. 8.
Figure 10:
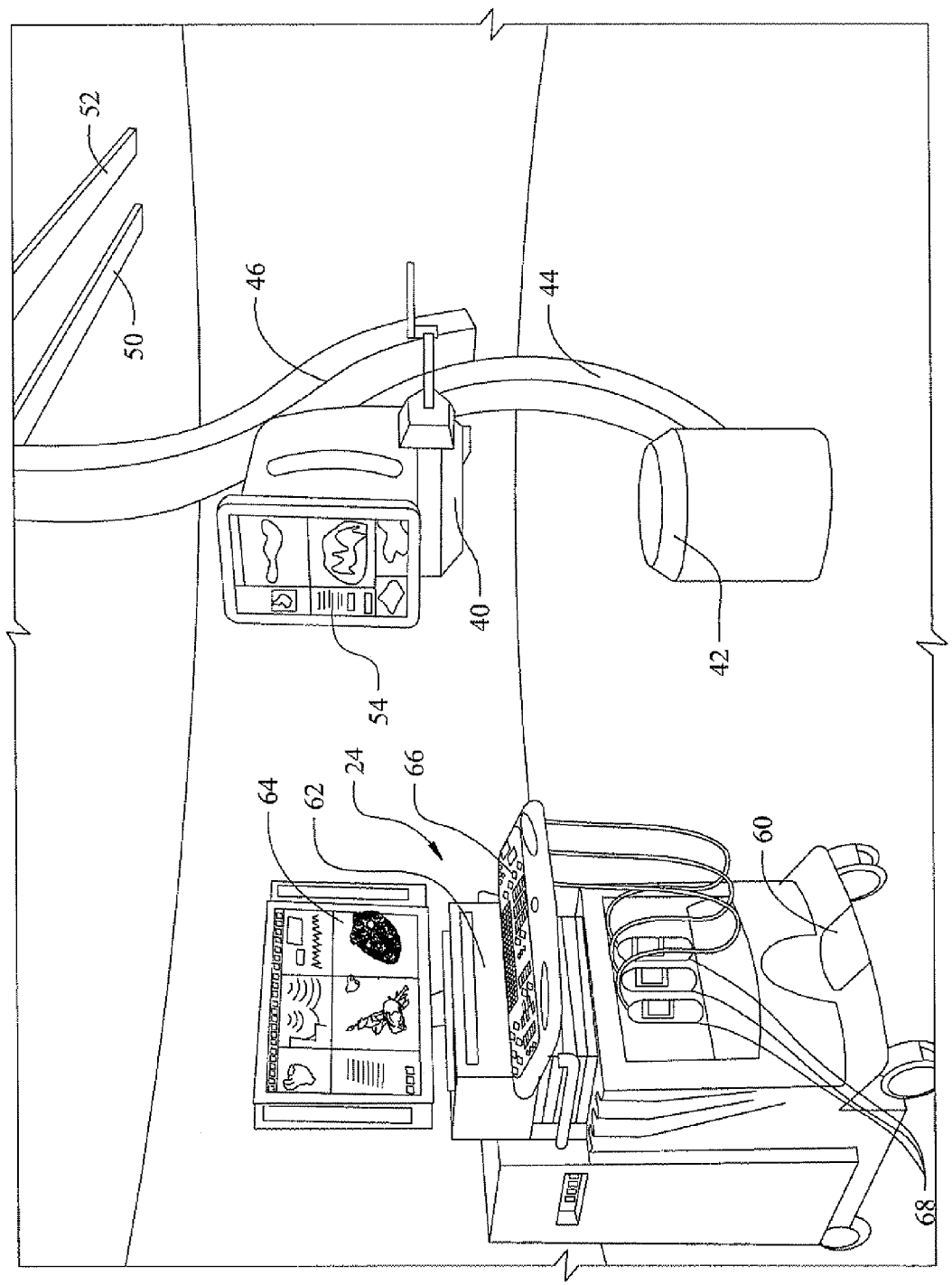
FIG. 10 is perspective view of an alternate construction of the procedure suite of the second embodiment, showing a ceiling mounted remote navigation system instead of a floor mounted remote navigation system.
Figure 11:
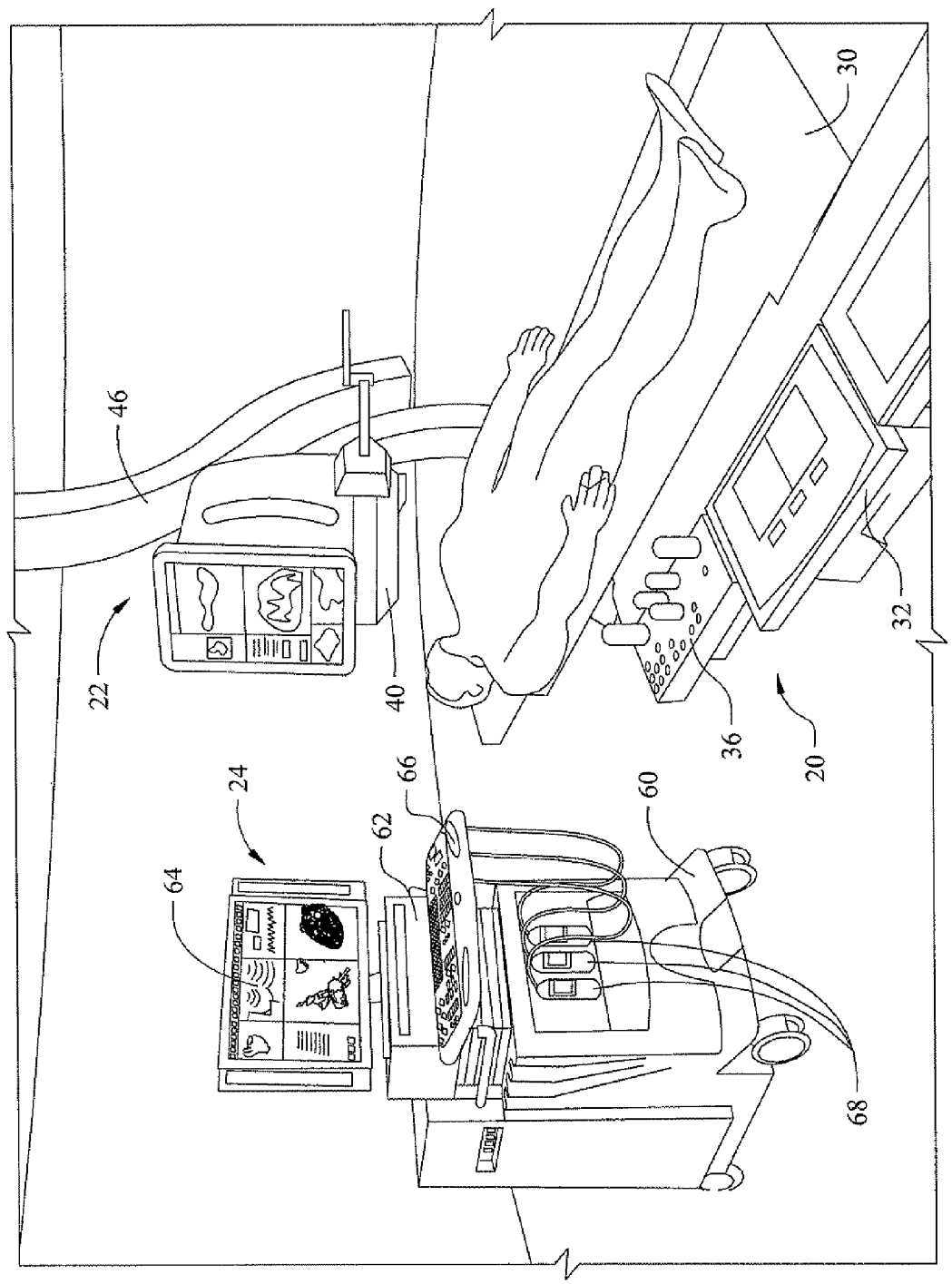
FIG. 11 is a perspective view of the alternate construction of the procedure suite of the second embodiment shown in FIG. 10, Other showing a subject on a subject support.
Figure 12:
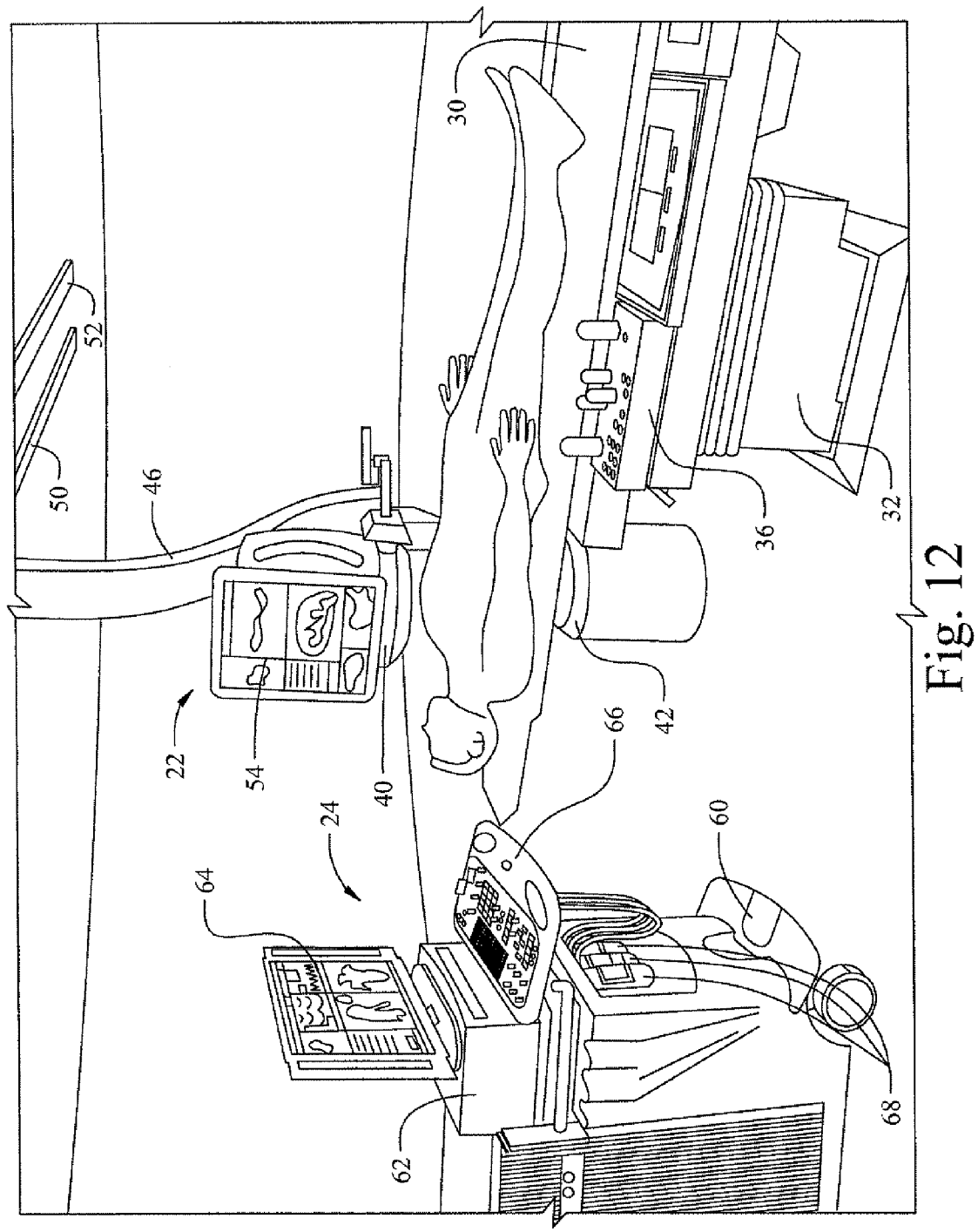
FIG. 12 is an enlarged perspective view of the procedure suite of the alternate construction of the second preferred embodiment, from a different view point than FIG. 11.

As shown the FIGS. 19-26, the magnet units 40 and 42 are preferably disposed above and below the subject. The magnet units 40 and 42 are mounted on a C-shaped frame 44 for maintaining the relative spacing and orientation of the units. The C-shaped frame 44 is positioned between the subject's head and neck on one side, so that the magnet units 40 and 42 can be disposed above and below an operating region in the subject's chest, while leaving the subject's sides unobstructed for access by the x-ray imaging system 26. As shown in FIGS. 19-26, the C-shaped frame is preferably mounted on a wheeled support 56 (FIGS. 5 and 6), which can roll in a track 58 (FIG. 5) in the floor. While a track 58 is not essential, it makes it easier to move the remote navigation unit, and to control the motion and position of remote navigation system 22 as it is being moved. (Alternatively, as described above, the remote navigation system 22 can be suspended from a bracket carried on a cart on ceiling tracks. While an overhead system would be satisfactory for moving the system 22 within the suite, it would generally be less desirable to extend ceiling tracks between suites.

The remote navigation system 22 includes at least a display 54 mounted adjacent the magnet unit 40. The display 54 may be a simple LCD or similar flat panel display for displaying information from the computer controlling the remote navigation system, and/or other information such as from the ultrasonic imaging system 24 or the x-ray imaging system 26. The display 54 may be a touch screen display to facilitate inputs to control the remote navigation system 22, and to manipulate the images displayed on the display. A speaker and/or a microphone may be integrated with the display as described above.

The external ultrasound imaging system 24 is preferably mounted on a wheeled cart 60 and includes a computer 62 with a display 64 and an input device such as a keyboard 66. One or more ultrasound transducers 68 are provided to ultrasonically image the operating region of a subject on the support 20. In addition one or more inputs (not shown) can be provided for connecting to ultrasonic catheters for internal ultrasonic imaging of the operating region in the subject.

The x-ray imaging system 26 is preferably a conventional x-ray imaging system comprising at least one x-ray source 70 and at least one x-ray receiver 72, mounted on a C-arm 74. The C-arm 74 is preferably a conventional C-arm that allows the C-arm to pivot about a generally horizontal axis to allow the physician or other health care professional to change the imaging angle. Other conventional movements to provide additional imaging angles can also be provided, as is known.

With the positioning and arrangement of the remote navigation system 22 and the x-ray imaging system 26, x-ray imaging can be used during the procedure if desired, to conduct the procedure or to simply periodically check on the progress of the procedure being conducting using some other imaging system, such as ultrasound. This arrangement also allows the navigation system 22 to be removed from the vicinity of the subject support 20, so that the x-ray imaging system 26 can be used conventionally, and even permits the navigation system 22 to be moved for use in other procedure suites.

Figure 22:
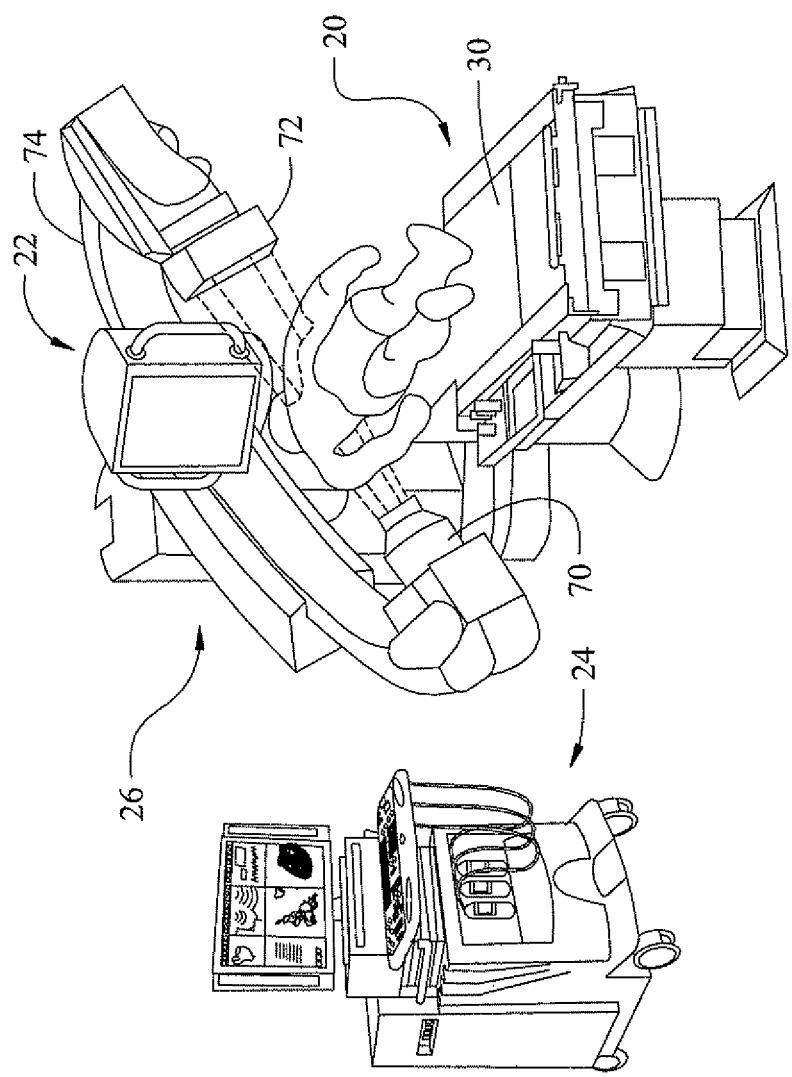
FIG. 22 is perspective view of the procedure suite shown in FIG. 19, showing the fluoroscopic imaging system positioned to provide a 60° LAO image.
Figure 23:
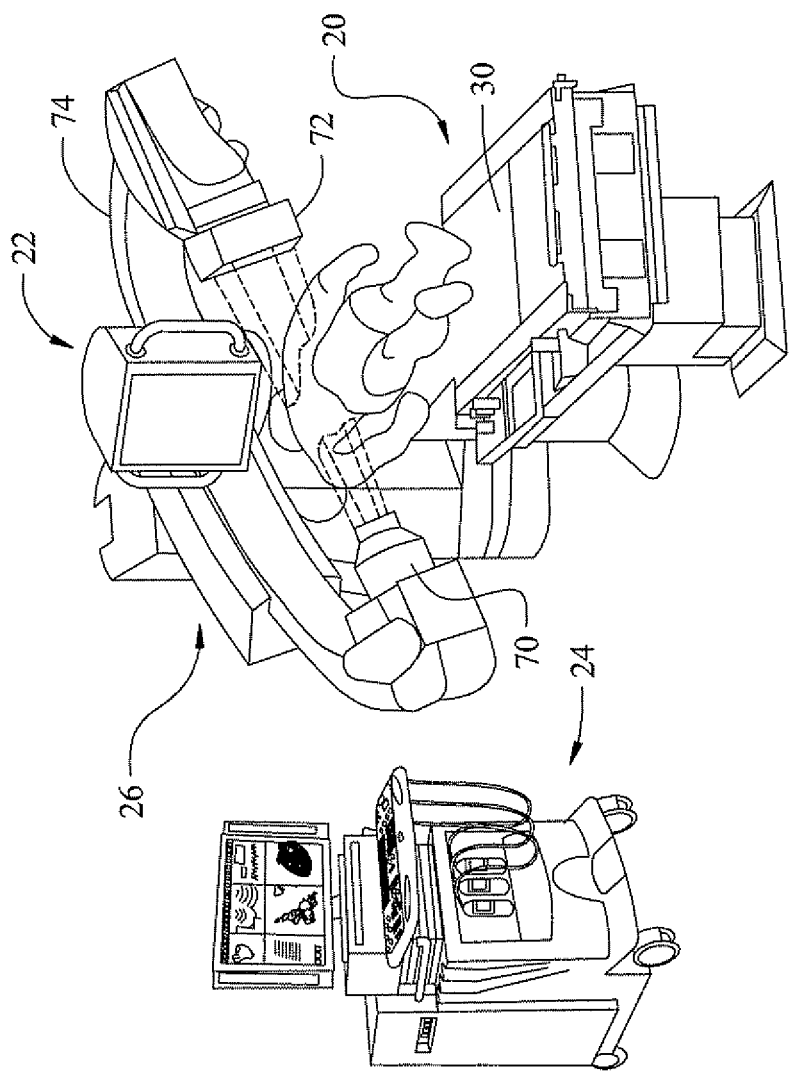
FIG. 23 is a perspective view of the procedure suite shown in FIG. 19, showing the fluoroscopic imaging system positioned to provide a 70° LAO image.
Figure 24:
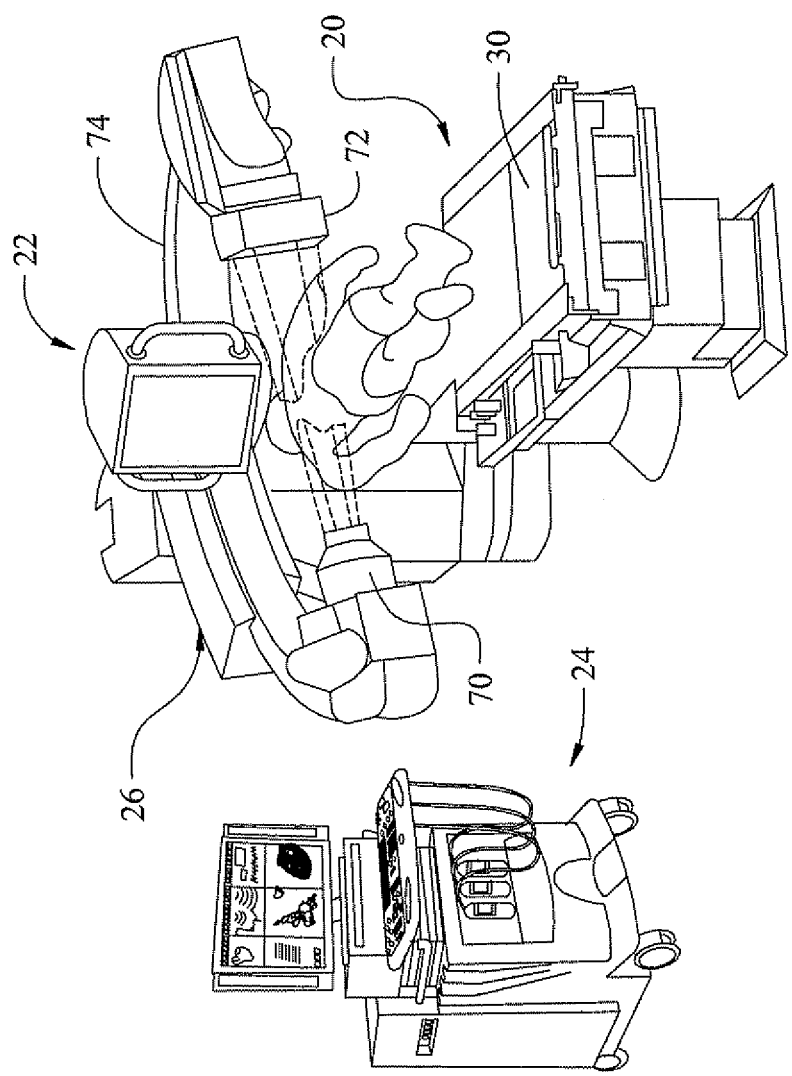
FIG. 24 is a perspective view of the procedure suite shown in FIG. 19, showing the fluoroscopic imaging system positioned to provide a 80° LAO image.
Figure 25:
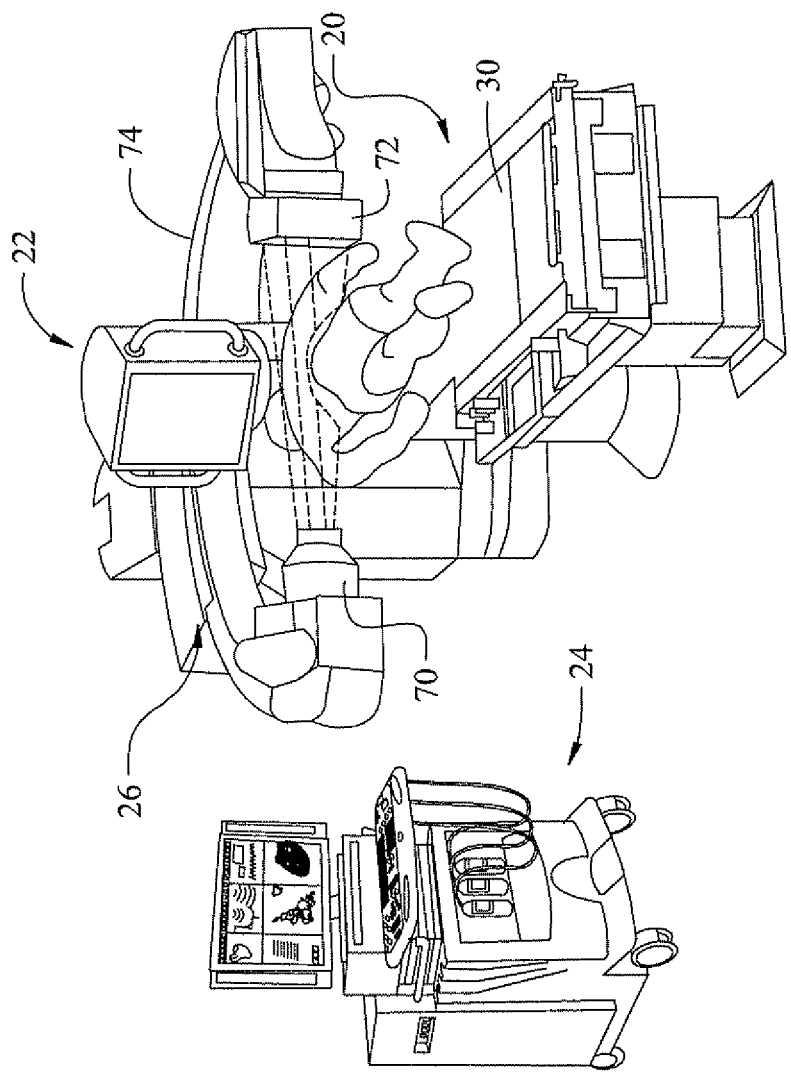
FIG. 25 is a perspective view of the procedure suite shown in FIG. 19, showing the fluoroscopic imaging system positioned to provide a 90° LAO image.
Figure 26A:
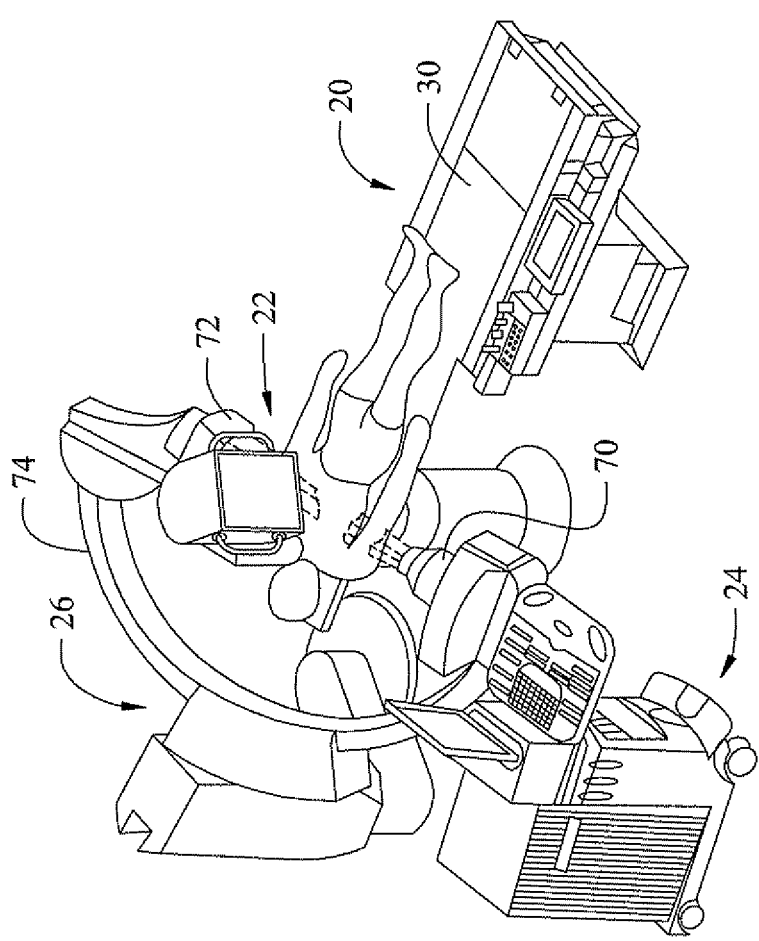
FIG. 26A is a perspective view of above of the procedure suite shown in FIG. 19, illustrating the position of the navigation system and the imaging system immediately after the end of the procedure.
Figure 26B:
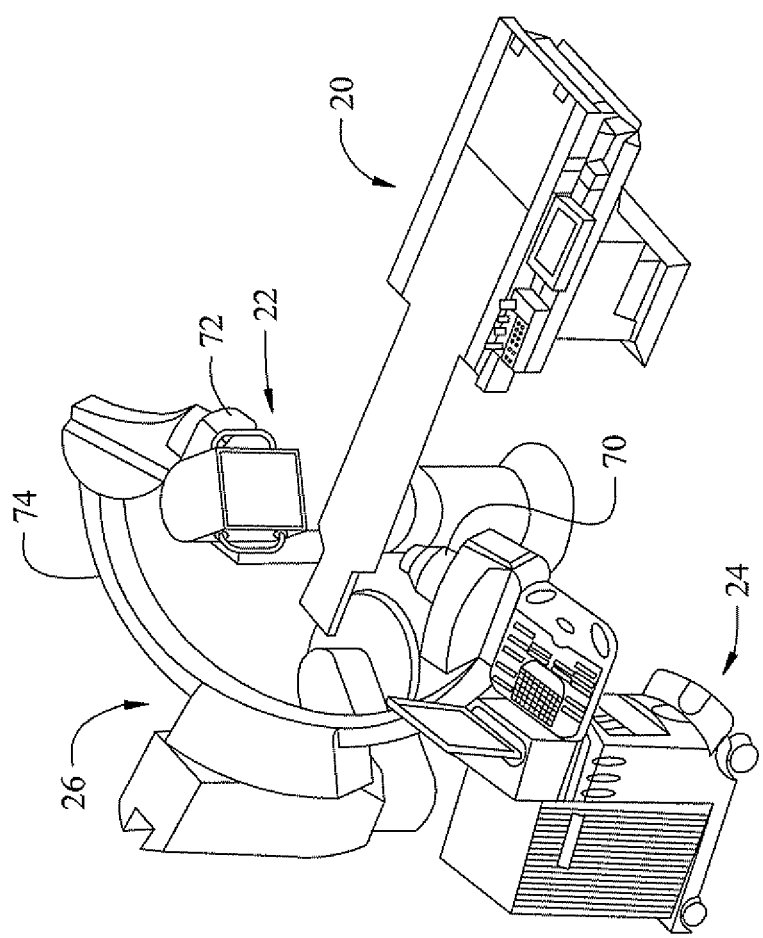
FIG. 26B is a perspective view of the procedure suite after removal of the subject from the subject support.
Figure 26C:
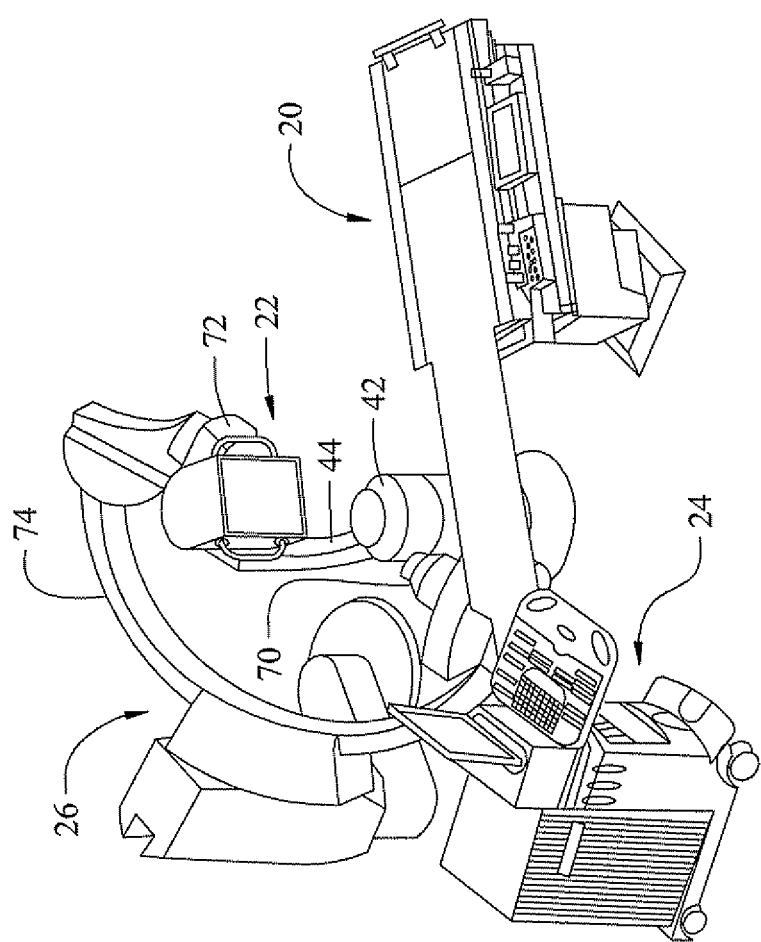
FIG. 26C is a perspective view of the procedure suite showing the subject support rotated to provide clearance for moving the navigation system.
Figure 26D:
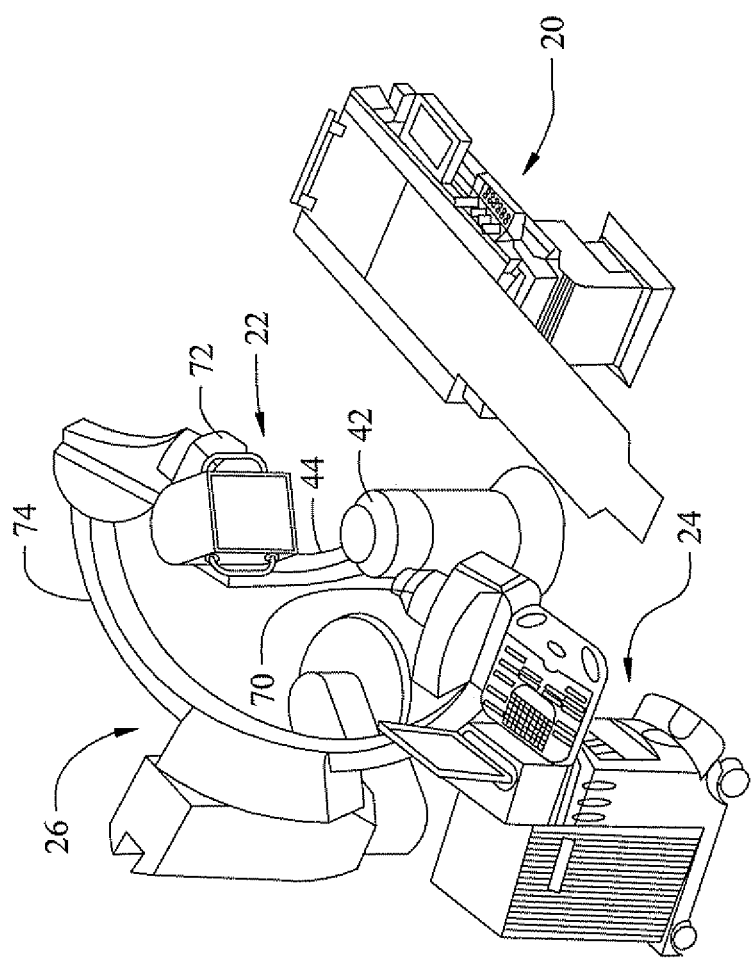
FIG. 26D is a perspective view of the procedure suite showing the subject support rotated 90 from its procedure orientation.
Figure 26E:
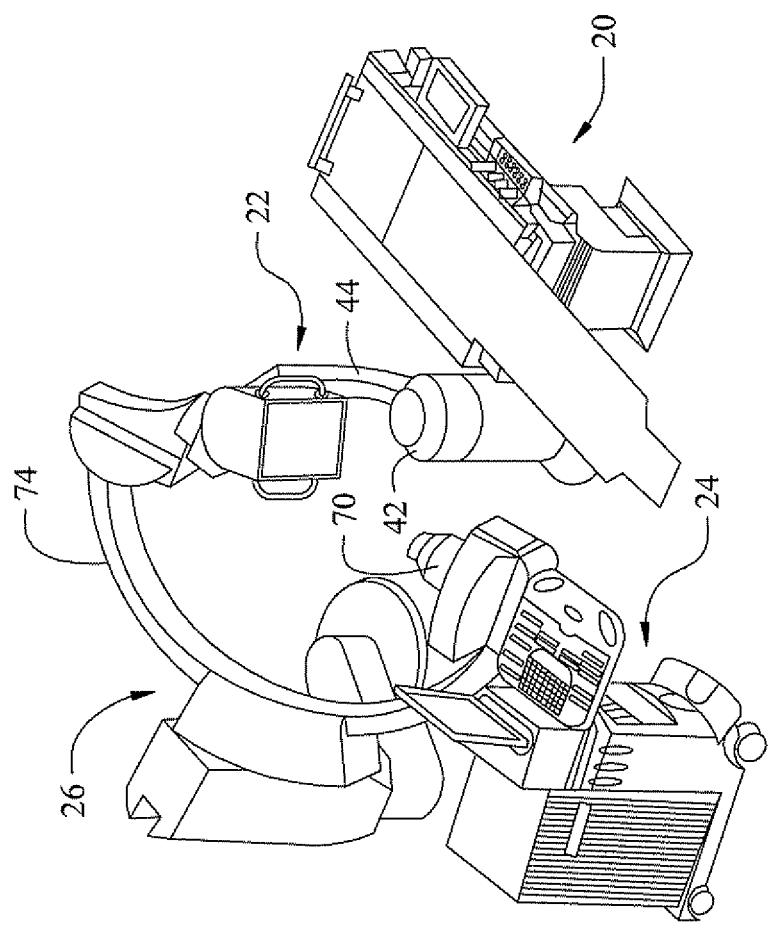
FIG. 26E is a perspective view of the procedure suite showing the remote navigation system moved toward the subject support to clear the imaging apparatus.
Figure 26F:
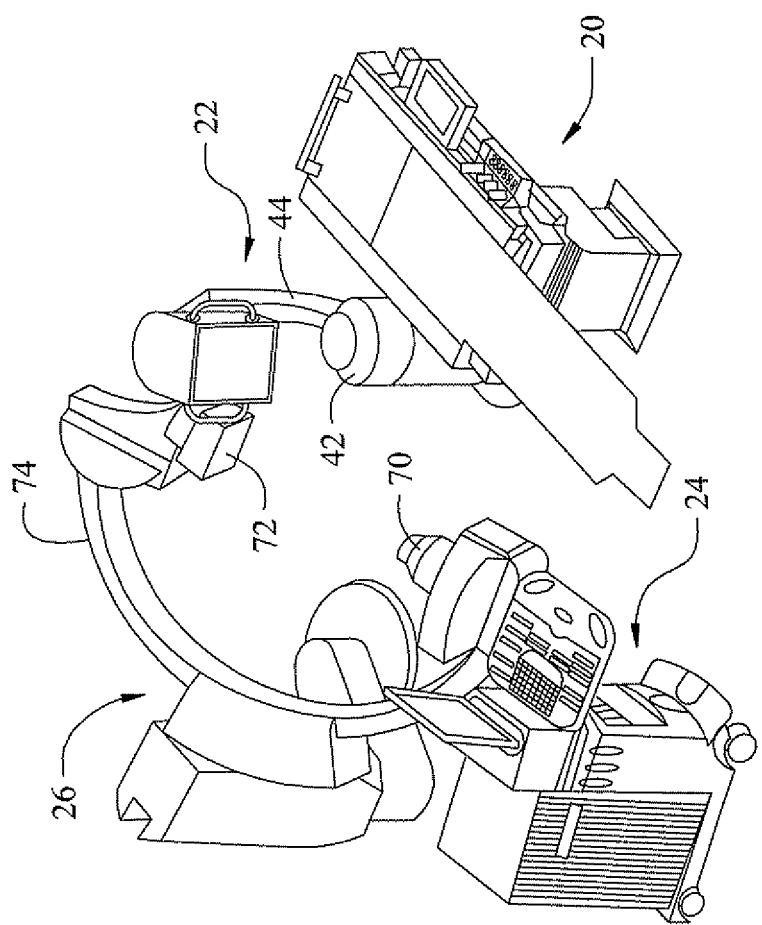
FIG. 26F is a perspective view of the procedure suite showing the magnet moving parallel to the subject support away from the imaging system.
Figure 26G:
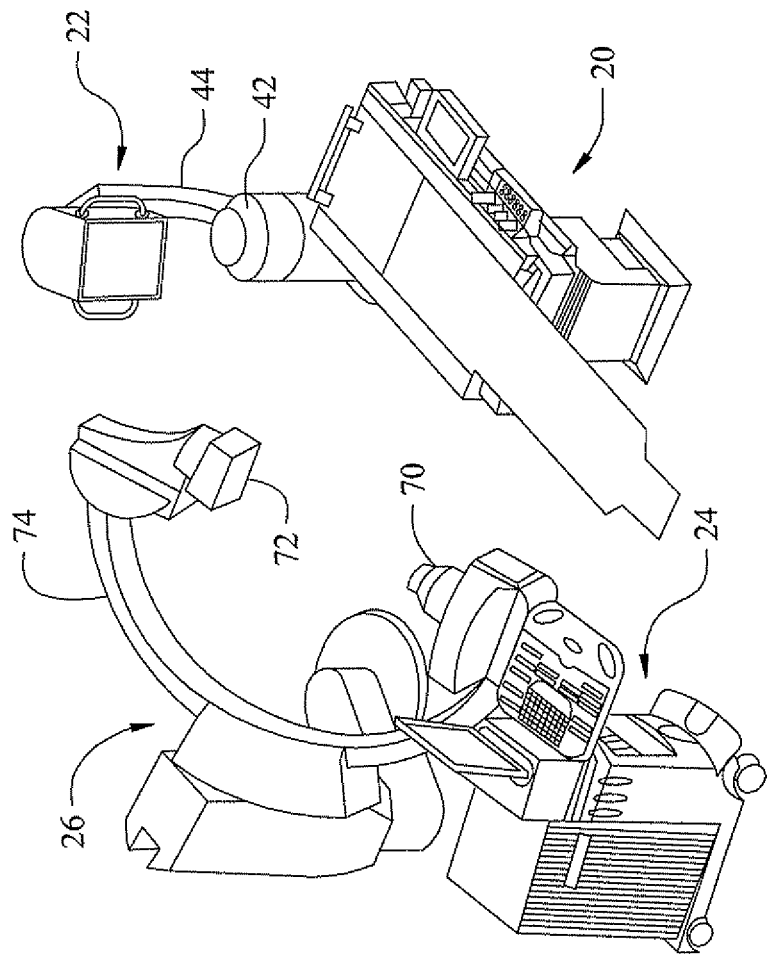
FIG. 26G is a perspective view of the procedure suite showing the remote navigation system moved away from the imaging system.
Figure 26H:
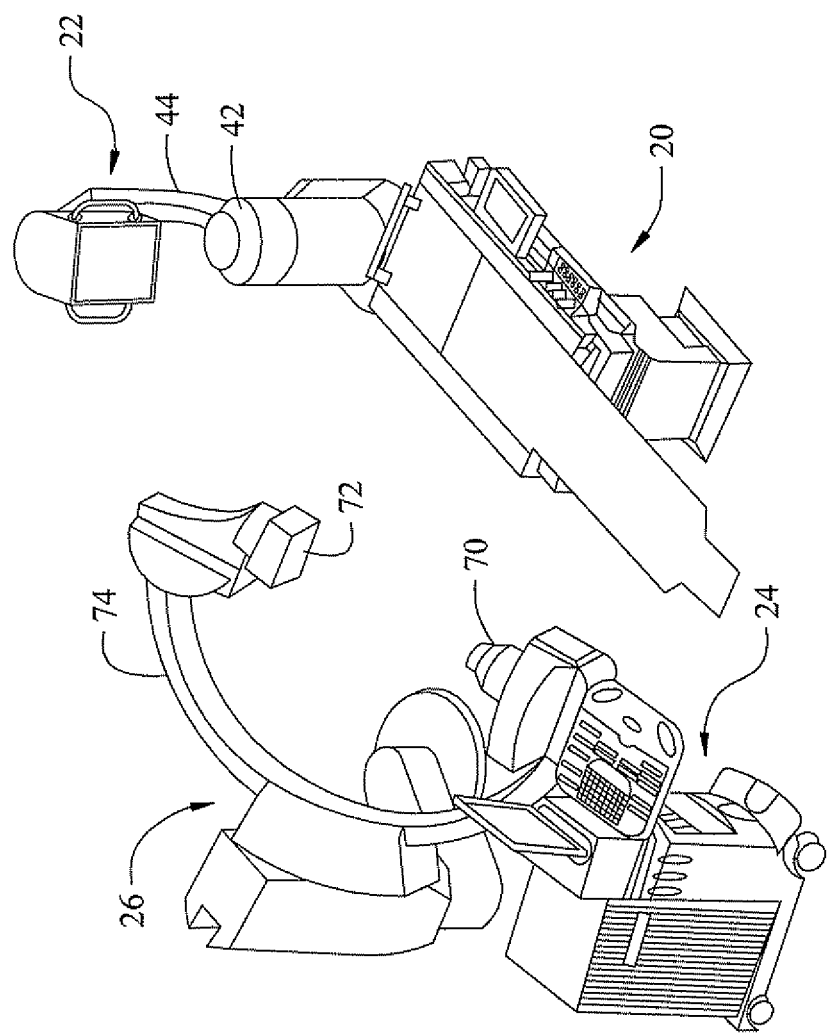
FIG. 26H is a perspective view of the procedure suite showing the remote navigation system moved to a safe parked position.
Figure 26I:
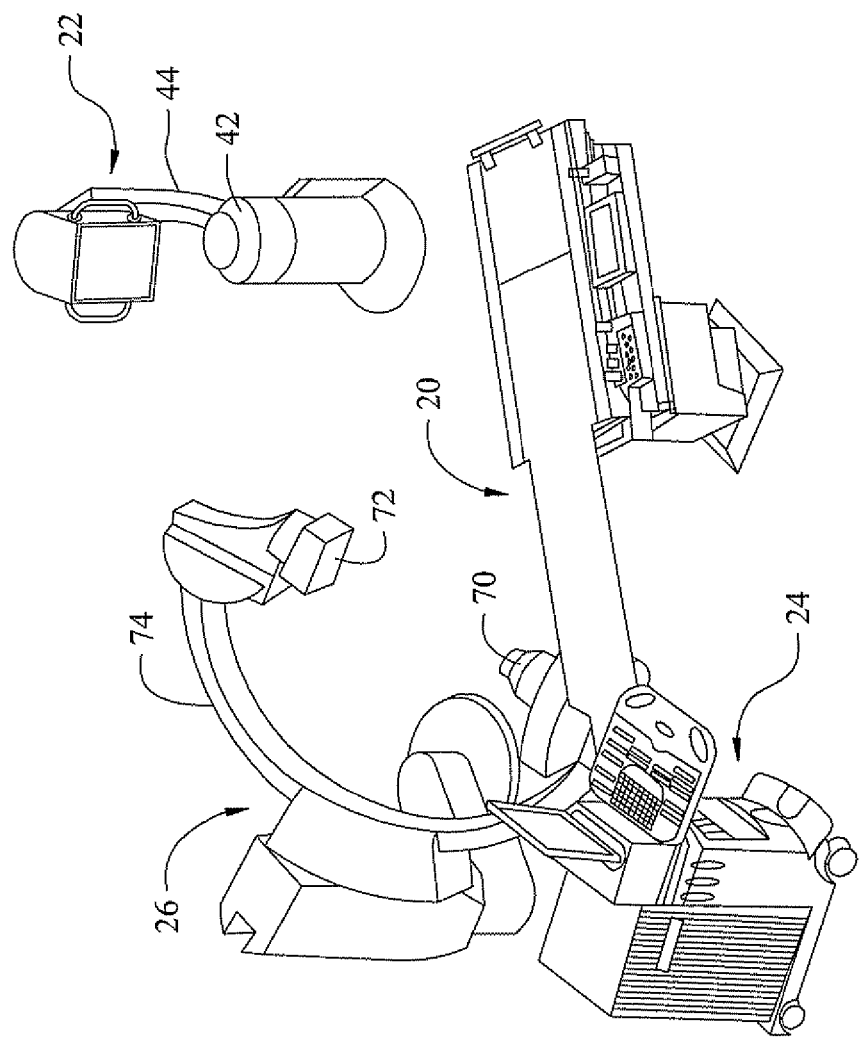
FIG. 26I is a perspective view of the procedure suite showing the subject support being rotated back into operating position.
Figure 26J:
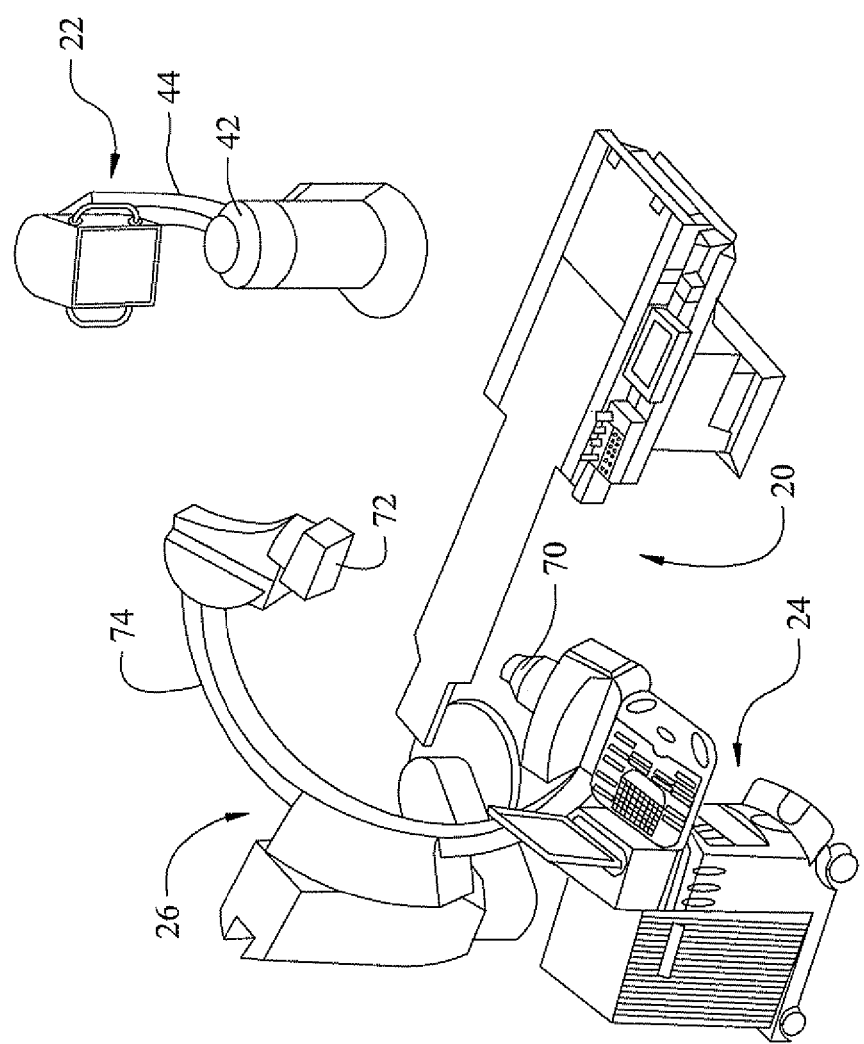
FIG. 26J is a perspective view of the procedure suite showing the subject support back into operating position.
Figure 26K:
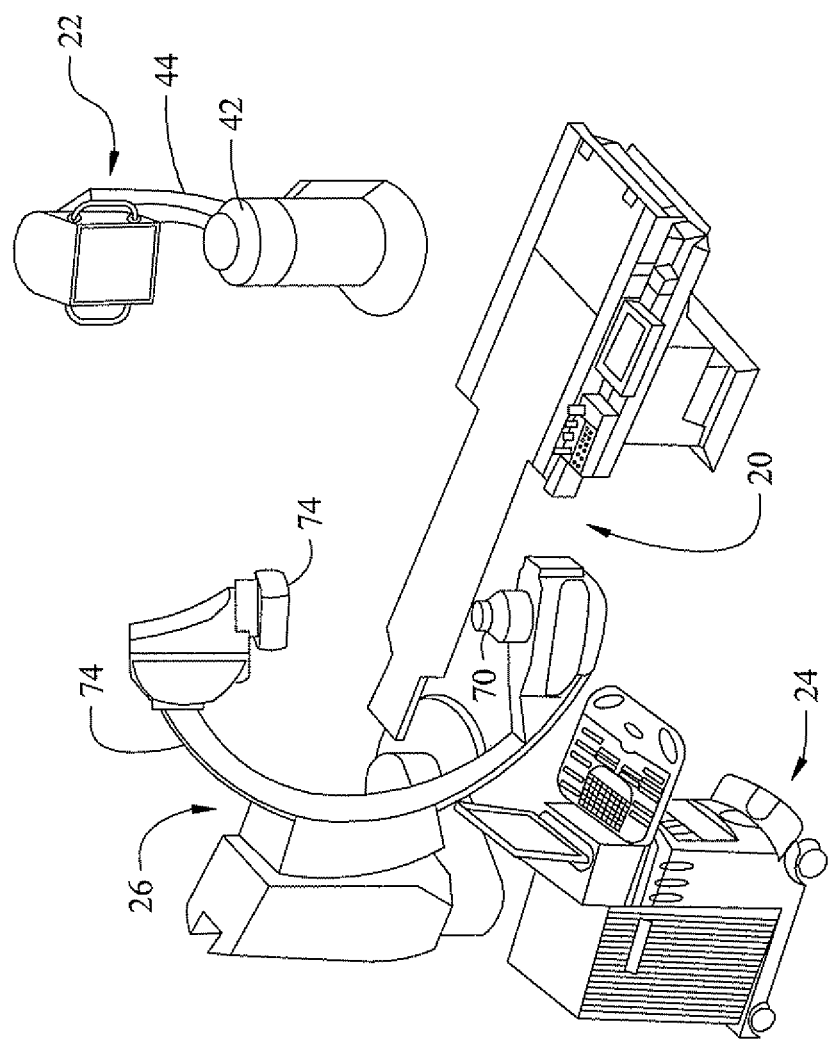
FIG. 26K is a perspective view of the procedure suite showing the suite ready for a procedure without the remote navigation system.

FIG. 22-25 illustrate the range of imaging possible with this configuration of the procedure suite, FIG. 22 showing 60° LAO imaging, FIG. 23 showing 70° LAO imaging, FIG. 24 showing 80° LAO imaging, and FIG. 25 showing 90° LAO imaging. With some manipulation it is also possible to provide RAO imaging. To this end, navigation system 22 may be designed to temporarily tilt, or it may be designed with a permanent tilt to reduce interference and increase the clearance for the x-ray imaging system 26. There are competing considerations in the tilting of the navigation system, because this tends to increase the distance between the magnet units 40 and 42, which requires larger magnets in the units to provide the same field strength.

FIG. 26 illustrates one possible method of moving the navigation system into and out of position relative to a standard x-ray imaging system. FIG. 26A illustrates the configuration of the procedure suite immediately after a procedure is completed. As shown in FIG. 26B, the subject is removed from the subject support 20. As shown in FIG. 26C, the subject support is rotated (this is a motion typically provided by subject supports in an imaging system). The rotation continues until the subject support has rotated 90° from its procedure position, shown in FIG. 26D. As shown in FIG. 26E, the remote navigation system 22 is moved toward the subject support 22 to clear the imaging apparatus. As shown in FIGS. 26F and 26G the remote navigation system 22 is moved parallel to the subject support 20 away from the imaging system, until as shown in FIG. 26H, it is clear of the subject support 20. Then, as shown in FIGS. 26I, 26X, and 26K, the subject support is rotated back into its operative position, so that the imaging system can be used conventionally.

What is claimed is:

1. A method of operating a remote navigation system that moves the distal end of a medical device in an operating region in a subject using as reference internally acquired ultrasound imaging with a localized ultrasound imaging catheter and system, the method comprising:
ultrasonically imaging the operating region using an ultrasound imaging system on an ultrasound imaging catheter in the operating region to obtain a generally planar ultrasound image;
registering the ultrasonic imaging system relative to the remote navigation system by using localization information corresponding to the ultrasound imaging catheter, and thence computing a spatial mapping between the remote navigation system and the ultrasound imaging system;
fusing the generally planar ultrasound image with three dimensional pre-operative data on the remote navigation system; and
using computer-controlled remote navigation to navigate the medical device to a target location selected on the generally planar ultrasound image.

2. A method of operating a remote navigation system that moves the distal end of a medical device in an operating region in a subject using as reference internally acquired ultrasound imaging from an ultrasound imaging system on an ultrasound imaging catheter, the method comprising:
automatically reorienting the ultrasound imaging catheter with a robotic mechanism as the medical device is steered by the remote navigation system to position the ultrasound imaging catheter such that the medical device stays within the imaging field-of-view of the ultrasound system on the ultrasound imaging catheter.

3. A method of operating a remote navigation system that moves the distal end of a medical device in an operating region in a subject using as reference internally acquired ultrasound imaging from an ultrasound imaging system on an ultrasound imaging catheter, the method comprising: computing and displaying a re-orientation of the ultrasound imaging catheter that will maintain the medical device in the field-of-view of the ultrasound imaging system as the medical device is steered by the remote navigation system.

4. A method of operating a remote navigation system that moves the distal end of a medical device in an operating region in a subject using as reference internally acquired ultrasound imaging from an ultrasound imaging system on a localized ultrasound imaging catheter, the method comprising:
ultrasonically imaging the operating region with the ultrasound imaging system on the ultrasound catheter;
registering the ultrasonic imaging system relative to the remote navigation system by using localization information corresponding to the ultrasound imaging catheter, and thence computing a spatial mapping between the remote navigation system and the ultrasound imaging system;
fusing three dimensional pre-operative image data with the ultrasound image data to provide additional anatomical context; and
navigating the medical device remotely with the remote navigation system using the fused data as additional reference.

5. A method of operating a remote navigation system that orients the distal end of a medical device in an operating region in a subject using as reference internally acquired ultrasound imaging from an ultrasound imaging system on an ultrasound imaging catheter, the method comprising: ultrasonically imaging the operating region with the ultrasound imaging system; registering the ultrasonic imaging system relative to the remote navigation system by marking two points in the distal portion of the ultrasound catheter on a pair of X-ray images, as well as an additional third point in the pair of X-ray images, marking similar points in the ultrasound image, and thence determining a spatial mapping between the remote navigation system and the ultrasound imaging system; fusing three dimensional pre-operative image data with the ultrasound image data to provide additional anatomical context; and
navigating the medical device remotely with the remote navigation system using the fused data as additional reference.

6. A method of operating a remote navigation system that moves the distal end of a medical device in an operating region in a subject using as reference internally acquired ultrasound imaging with an ultrasound imaging catheter and system, the method comprising: automatically reorienting the ultrasound imaging catheter as the medical device is moved to anatomical targets of interest such that the medical device remains within the imaging field-of-view of the ultrasound imaging system.

7. A method of navigating the distal end of a medical device through a body lumen, the method comprising:
ultrasonically imaging a portion of the body lumen surrounding the distal end of the medical device; and
comparing the ultrasound image of the portion of the body lumen with a three dimensional reconstruction of the body lumen registered to a Cartesian frame of a remote navigation system to obtain a location of the distal end of the medical device relative to the three dimensional reconstruction; using the location to obtain registration of the ultrasonic image with the Cartesian frame of the navigation system.

8. The method according to claim 7 further comprising using the extended length of the medical device to facilitate the comparison between the image of the portion of the body lumen and the three dimensional reconstruction of the body lumen.

9. The method according to claim 8 wherein the extended length of the medical device is used to identify locations in the three dimensional reconstruction for comparison with the image of the portion of the body lumen.

10. A method of navigating the distal end of a medical device through a body lumen, the method comprising:
ultrasonically imaging a portion of the body lumen surrounding the distal end of the medical device;
displaying an image of the portion of the body lumen surrounding the distal end of the medical device; and
placing the displayed image in anatomical context by comparing the image of the portion of the body lumen with a three dimensional reconstruction of the body lumen registered to the Cartesian frame of a remote navigation system to locate the distal end of the medical device relative to the three dimensional reconstruction;
using the location to obtain registration of the ultrasonic image with the Cartesian frame of the navigation system.

11. The method according to claim 10 further comprising using the extended length of the medical device to facilitate the comparison between the comparing the image of the portion of the body lumen with a three dimensional reconstruction of the body lumen.

12. The method according to claim 11 wherein the extended length of the medical device is used to identify locations in the three dimensional reconstruction for comparison with the image of the portion of the body lumen.

13. The method according to claim 12 further comprising displaying the current location of the distal end of the medical device in a three-dimensional model of the body lumen.

14. The method according to claim 12 further comprising accepting input of a selected direction of orientation by clicking on the displayed image of the portion of the body lumen surrounding the distal end of the medical device, and orienting the distal end of the medical device in the selected direction.

\* \* \* \* \*